(12) United States Patent
Boylan et al.

(10) Patent No.: US 8,741,889 B2
(45) Date of Patent: Jun. 3, 2014

(54) METHOD OF TREATING NON-SMALL CELL LUNG CANCER AND COLON CANCER WITH GAMMA-SECRETASE INHIBITOR

(75) Inventors: John Frederick Boylan, Bedminster, NJ (US); Leopoldo Ladores Luistro, Nutley, NJ (US); Kathryn Elizabeth Packman, Bloomfield, NJ (US)

(73) Assignee: Hoffmann-La Roche Inc, Nutley, NJ (US)

( * ) Notice: Subject to any disclaimer, the term of this patent is extended or adjusted under 35 U.S.C. 154(b) by 0 days.

(21) Appl. No.: 13/450,629

(22) Filed: Apr. 19, 2012

(65) Prior Publication Data

US 2013/0281437 A1    Oct. 24, 2013

Related U.S. Application Data

(63) Continuation of application No. 12/348,464, filed on Jan. 5, 2009, now abandoned.

(60) Provisional application No. 61/020,447, filed on Jan. 11, 2008.

(51) Int. Cl.
*C07D 313/06* (2006.01)
*A61K 31/55* (2006.01)
*A61P 35/04* (2006.01)

(52) U.S. Cl.
USPC ............ 514/212.04; 514/19.3; 514/212.07; 514/221; 514/450; 540/517; 540/522; 540/523; 549/354

(58) Field of Classification Search
USPC ............ 514/212.04, 19.3, 212.07, 221, 450; 540/517, 522, 523; 549/354
See application file for complete search history.

(56) References Cited

U.S. PATENT DOCUMENTS

| 7,160,875 B2 | 1/2007 | Flohr et al. | |
| 2006/0122168 A1* | 6/2006 | Flohr et al. | 514/211.06 |
| 2006/0251617 A1* | 11/2006 | Denis-Mize et al. | 424/85.2 |

FOREIGN PATENT DOCUMENTS

| WO | 2005023772 | 3/2005 | |
| WO | WO 2005/023772 | * 3/2005 | ........... C07D 223/18 |
| WO | 2006123184 | 11/2006 | |
| WO | 2007/100895 | 9/2007 | |

OTHER PUBLICATIONS

Feruse et al. In Journal of Clinical Oncology, 7:2692-2699 (1999).*
(International Search Report for PCT/EP2009/050047 Mar. 18, 2009).
(Chinese Office Action n Corres. Appl. CN2009 80101733.1 Jun. 2, 2011).
Notice from National Registry of Costa Rica (Jan. 14, 2011).
(Translation of Korean Office Action in Corres Korean App 20107014569 Nov. 29, 2013).
Kim, Yong-tae, "Chemotherapy for pancreatic cancer" Other Korean Society of Gastroenterology 2006 Autumn Conference, (2006).

* cited by examiner

*Primary Examiner* — Savitha Rao

(57) ABSTRACT

The present invention provides a method for treating a patient having cancer comprising administering to the patient a therapeutically effective amount of compound (1), or a pharmaceutically acceptable salt thereof, having the formula:

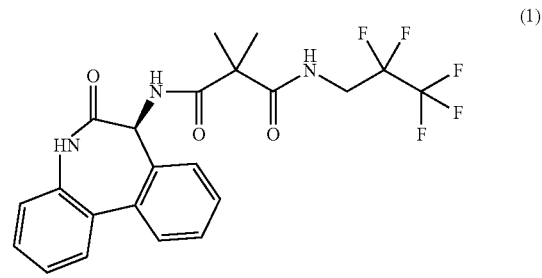

The present invention also provides a kit containing the above compound.

15 Claims, No Drawings

METHOD OF TREATING NON-SMALL CELL LUNG CANCER AND COLON CANCER WITH GAMMA-SECRETASE INHIBITOR

PRIORITY TO RELATED APPLICATION(S)

This application is a continuation of U.S. application Ser. No. 12/348,464, filed, Jan. 5, 2009, now pending, which claims the benefit of U.S. Provisional Application No. 61/020,447, filed Jan. 11, 2008, which is hereby incorporated by reference in its entirety.

FIELD OF THE INVENTION

The present invention provides a method for treating a patient having cancer comprising administering to the patient a therapeutically effective amount of compound (1), or a pharmaceutically acceptable salt thereof, having the formula:

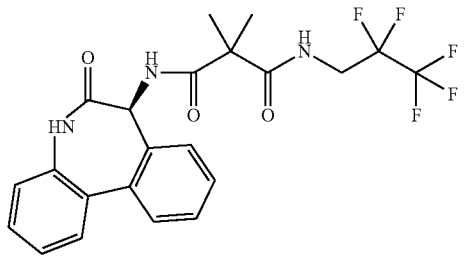

(1)

The present invention also provides a kit containing compound (1).

BACKGROUND OF THE INVENTION

Cancer remains a major cause of mortality and morbidity worldwide, despite recent success with drugs that provide survival benefit to patients. For most solid tumors, there is still a high rate of tumor recurrence and metastases associated with poor prognosis. Currently available drugs include cytotoxic chemotherapeutics, antiangiogenic agents, and targeted agents. The clinical benefit achieved with most of the currently available anticancer drugs is limited due to either development of drug resistance or intolerable toxicities that may affect a variety of organs (e.g., hematological toxicities, hepatotoxicity, nephrotoxicity, and neurotoxicity).

Cancer is a disease characterized by uncontrolled proliferation. Advances in understanding the signals that drive cancer are being made. During development and tissue remodeling, pluripotent stem cells serve as the source for differentiating cells to give rise to non-proliferating specialized cell types. A link between the characteristics of these stem cells and the rapid uncontrolled proliferation of tumors is becoming clear. One of the major developmental signaling axes is the Notch pathway. Notch signaling regulates cell-fate by mediating the differentiation of progenitor cells during development and self-renewal of adult pluripotent stem cells. Notch functions to maintain progenitor cells in a pluripotent rapidly proliferating state. The Notch pathway plays an important role in development differentiation and processes of hematopoiesis and lymphopoiesis. It is involved in generation, proliferation and differentiation of hematopoietic stem cells during embryonic development.

Notch gene amplification, chromosomal translocation or mutations lead to elevated Notch signaling, thereby imparting a tumor growth advantage by keeping tumor cells in a stem cell-like proliferative state. Therefore, there is a very strong correlation between mutation in the Notch signaling pathway and pathogenesis of malignancies.

The Notch proteins, represented by four homologs in mammals (Notch1, Notch2, Notch3, and Notch4), interact with ligands Delta-like 1, Delta-like 3, Delta-like 4, Jagged 1, and Jagged 2. After ligand binding, Notch receptors are activated by serial proteolytic cleavage events including intramembranous cleavage regulated by γ-secretase. Such a γ-secretase-processed Notch becomes active as a form called intracellular subunits (ICN). The ICN translocates to the nucleus and forms part of a large transcription complex involving the CSL (CBF-1, Suppressor of hairless, Lag) transcriptional regulator directly altering the expression of key proliferation- and differentiation-specific genes.

In addition, γ-secretase is involved in the intramembrane proteolytic processing of several other proteins, including amyloid precursor protein [APP], CD44 stem cell marker, and HER4 [ErbB4]). Blocking Notch signaling via γ-secretase inhibition produces a slower growing, less transformed, phenotype in human cancer cells in vivo. Importantly, this phenotype remains stable in the absence of further dosing. This type of novel treatment approach holds the potential to make cancer a more manageable disease without the strong side-effects of traditional cytotoxic drugs.

2,2-Dimethyl-N—((S)-6-oxo-6,7-dihydro-5H-dibenzo[b,d]azepin-7-yl)-N'-(2,2,3,3,3-pentafluoro-propyl)-malonamide (1) is disclosed in WO 2005/023772 as useful for the treatment of Alzheimer's disease.

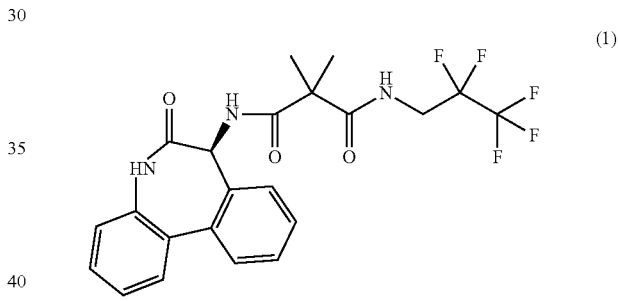

(1)

Therefore, there is a need to develop new drugs/chemotherapy protocols to further improve the treatment available for cancer patients.

SUMMARY OF THE INVENTION

The present invention provides a method for treating a patient having cancer comprising administering to the patient a therapeutically effective amount of compound (1), or a pharmaceutically acceptable salt thereof, having the formula:

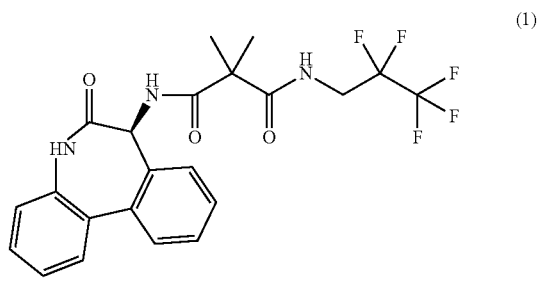

(1)

The present invention also provides a method for treating a patient having cancer comprising administering to the patient a therapeutically effective amount of compound (1), or a pharmaceutically acceptable salt thereof, having the formula:

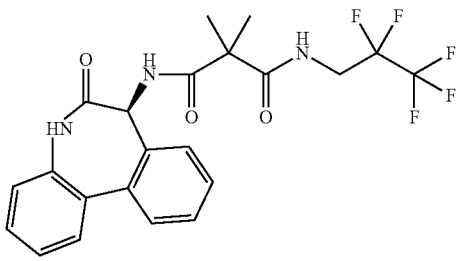

(1)

wherein compound (1) is administered once daily on days 1, 2, 3, 8, 9, and 10 of a 21 day cycle in an amount of from about 400 ng-hr/ml to about 9000 ng-hr/ml.

The present invention further provides a method for treating a patient having cancer comprising administering to the patient a therapeutically effective amount of compound (1), or a pharmaceutically acceptable salt thereof, having the formula:

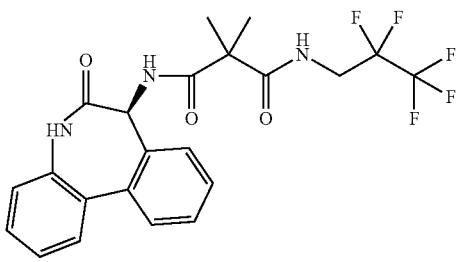

(1)

wherein compound (1) is administered once daily on days 1-7 of a 21 day cycle in an amount of from about 400 ng-hr/ml to about 9000 ng-hr/ml.

The present invention still further provides a kit comprising one or more oral unit dosage forms, each unit containing from about 3 mg to about 300 mg of compound (1), or a pharmaceutically acceptable salt thereof, having the formula:

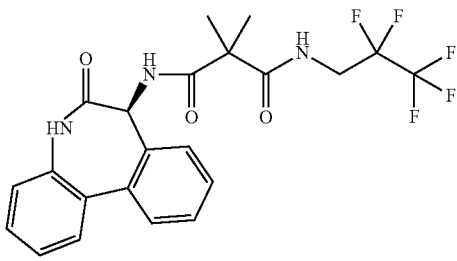

(1)

DETAILED DESCRIPTION OF THE INVENTION

The present invention provides novel methods of treating a patient having cancer comprising administering to the patient a therapeutically effective amount of compound (1), or a pharmaceutically acceptable salt thereof. Compound (1) is a potent and selective inhibitor of γ-secretase producing inhibitory activity of Notch signaling in tumor cells.

As used herein, the following terms have the meanings set out below.

The term "antineoplastic" means inhibiting or preventing the development, maturation or proliferation of malignant cells.

The term "area under the curve" (AUC) is the area under the curve in a plot of concentration of drug in plasma against time. AUC represents the total amount of drug absorbed by the body, irrespective of the rate of absorption. This is useful for the therapeutic monitoring of drugs. Measurement of the drug concentrations in a patient's plasma and calculation of the AUC is useful to guide the dosage of this drug. AUC becomes useful for knowing the average concentration over a time interval, AUC/t. AUC is generally expressed as (mass*time/volume), for example, ng-hr/ml.

The term "pharmaceutically acceptable," such as pharmaceutically acceptable carrier, excipient, etc., means pharmacologically acceptable and substantially non-toxic to the subject to which the particular compound is administered. The term "pharmaceutically acceptable salt" refers to conventional acid-addition salts or base-addition salts that retain the biological effectiveness and properties of the compounds of the present invention and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium, and quaternary ammonium hydroxides, such as for example, tetramethylammonium hydroxide. The term "pharmaceutically acceptable ester" of a compound means a conventionally esterified compound having a carboxyl group, which esters retain the biological effectiveness and properties of the compound. Chemical modification of a pharmaceutical compound (i.e., drug) into a salt is a technique well known to pharmaceutical chemists to obtain improved physical and chemical stability, hydroscopicity, and solubility of compounds. See, e.g., H. Ansel et. al., Pharmaceutical Dosage Forms and Drug Delivery Systems ($6^{th}$ Ed. 1995) at pp. 196 and 1456-1457.

The term "prodrug" refers to compounds, which undergo transformation prior to exhibiting their pharmacological effects. The chemical modification of drugs to overcome pharmaceutical problems has also been termed "drug latentiation." Drug latentiation is the chemical modification of a biologically active compound to form a new compound, which upon in vivo enzymatic attack will liberate the parent compound. The chemical alterations of the parent compound are such that the change in physicochemical properties will affect the absorption, distribution and enzymatic metabolism. The definition of drug latentiation has also been extended to include nonenzymatic regeneration of the parent compound. Regeneration takes place as a consequence of hydrolytic, dissociative, and other reactions not necessarily enzyme mediated. The terms prodrugs, latentiated drugs, and bioreversible derivatives are used interchangeably. By inference, latentiation implies a time lag element or time component involved in regenerating the bioactive parent molecule in vivo. The term prodrug is general in that it includes latentiated drug derivatives as well as those substances, which are converted after administration to the actual substance, which combines with receptors. The term prodrug is a generic term for agents, which undergo biotransformation prior to exhibiting their pharmacological actions.

The term "therapeutically effective amount" means an amount of drug, which is effective for producing a desired therapeutic effect upon administration to a patient, for example, to stem the growth, or result in the shrinkage, of a cancerous tumor.

The term "therapeutic index" is an important parameter in the selection of anticancer agents for clinical trial. Therapeutic Index takes into consideration the efficacy, pharmacokinetecs, metabolism and bioavailability of anticancer agents. See, e.g., J. Natl. Cancer Inst. 81(13): 988-94 (Jul. 5, 1989).

The term "tumor control" means that the perpendicular diameters of measurable lesions have not increased by 25% or more from the last measurement. See, e.g., World Health Organization ("WHO") Handbook for Reporting Results of Cancer Treatment, Geneva (1979).

The present invention provides a method for treating a patient having cancer comprising administering to the patient a therapeutically effective amount of compound (1), or a pharmaceutically acceptable salt thereof, having the formula:

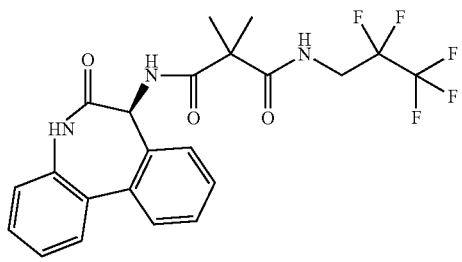

(1)

Compound (1) is a potent and selective inhibitor of γ-secretase, a key enzyme responsible for the cleavage and activation of Notch receptors. Dysregulation of Notch signaling due to gene amplification, chromosomal translocation, or mutations has been implicated in many types of cancers including leukemia, medullo- and glioblastoma, breast carcinoma, head and neck cancer, and pancreatic carcinoma. Preclinical evidence has shown that blockade of Notch signaling through inhibition of the proteolytic activity of γ-secretase results in deterring tumor growth in mouse xenograft models.

The therapeutically effective amount of compound (1) is an amount effective for producing a desired therapeutic effect upon administration to a patient to stem the growth, or result in the shrinkage, of a cancerous tumor. Preferably, the therapeutically effective amount of compound (1) is from about 400 ng-hr/ml to about 9000 ng-hr/ml, more preferably from about 1100 ng-hr/ml to about 4100 ng-hr/ml, and most preferably from about 1380 ng-hr/ml to about 2330 ng-hr/ml.

In one embodiment, the therapeutically effective amount of compound (1) is from about 400 ng-hr/ml to about 9000 ng-hr/ml, more preferably from about 1100 ng-hr/ml to about 4100 ng-hr/ml, and most preferably from about 1380 ng-hr/ml to about 2330 ng-hr/ml, administered over a period of up to about 21 days.

In another embodiment, compound (1) is administered once daily on days 1, 2, 3, 8, 9, and 10 of a 21 day cycle. In a preferred embodiment, compound (1) is administered once daily on days 1, 2, 3, 8, 9, and 10 of a 21 day cycle in an amount of from about 400 ng-hr/ml to about 9000 ng-hr/ml.

In yet another embodiment, compound (1) is administered once daily on days 1-7 of a 21 day cycle. In a preferred embodiment, compound (1) is administered once daily on days 1-7 of a 21 day cycle in an amount of from about 400 ng-hr/ml to about 9000 ng-hr/ml.

Preferably, compound (1) is in a pharmaceutical oral unit dosage form. The present method may also comprise additionally subjecting the patient to radiotherapy.

In a specific embodiment, the present invention provides a method for treating a patient having cancer comprising administering to the patient a therapeutically effective amount of compound (1), or a pharmaceutically acceptable salt thereof, having the formula:

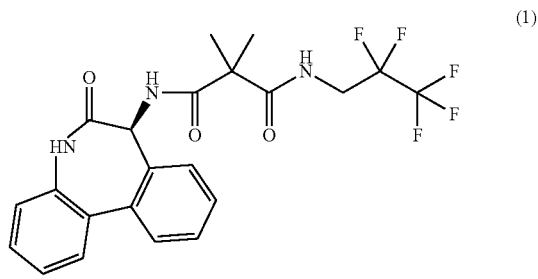

(1)

wherein compound (1) is administered once daily on days 1, 2, 3, 8, 9, and 10 of a 21 day cycle in an amount of from about 400 ng-hr/ml to about 9000 ng-hr/ml being repeated as long as the cancer remains under control.

In another specific embodiment, the present invention provides a method for treating a patient having cancer comprising administering to the patient a therapeutically effective amount of compound (1), or a pharmaceutically acceptable salt thereof, having the formula:

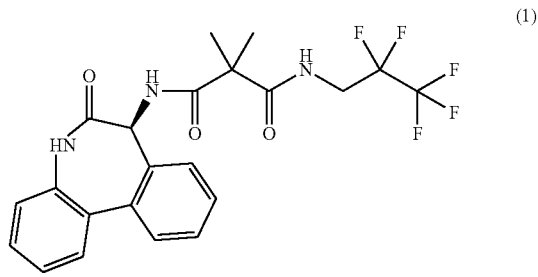 [SMILES: CC(C)(C(=O)NCC(F)(F)C(F)(F)F)C(=O)N[C@@H]1C(=O)Nc2ccccc2-c2ccccc21]

(1)

wherein compound (1) is administered once daily on days 1-7 of a 21 day cycle in an amount of from about 400 ng-hr/ml to about 9000 ng-hr/ml being repeated as long as the cancer remains under control.

In yet another specific embodiment, the present invention provides a kit comprising one or more oral unit dosage forms, each unit containing from about 3 mg to about 300 mg of compound (1), or a pharmaceutically acceptable salt thereof, having the formula:

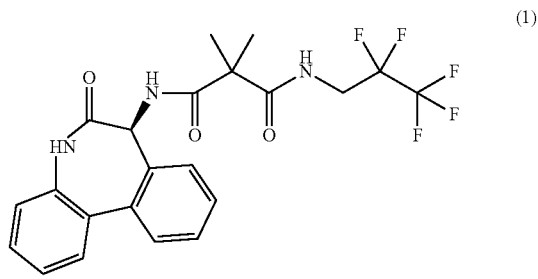

(1)

In this embodiment, the kit of may comprise oral unit dosage forms containing a sufficient number of units so that a patient can administer about 300 mg per day of compound (1), or a pharmaceutically acceptable salt thereof, for a period of about 21 days.

The dosage levels of each of the components may be modified by a physician to be lower or higher than that stated herein depending on the needs of the patient, and the reaction of the patient to the treatment. The dosages may be administered according to any dosage schedule determined by the physician in accordance with the requirements of the patient. For example, the dosages of each of the two components may be administered in single or in divided doses over a period of several days, or alternating daily schedules.

Preferably, treatment schedules are repeated every twenty one days, or as soon as permitted by recovery from toxicity, for so long as the tumor is under control and the patient tolerates the regiment or tumor regression. Preferably, these treatment cycles are repeated for a total of up to about eight cycles.

The methods of the present invention can be prepared according to the examples set out below. The examples are presented for purposes of demonstrating, but not limiting, the preparation of the compounds and compositions of this invention.

EXAMPLES

Example 1

Breadth of Antitumor Activity of Once Daily Oral Administration of Compound (1) in Human Tumor Xenografts in Nude Mice In a previous antitumor efficacy study, when compound (1) was administered orally to mice bearing A549 non-small cell lung carcinoma (NSCLC) xenografts, doses of 3, 10, or 30 mg/kg given once or twice daily for 14 (14+/7−) or 21 days resulted in significant and sustained tumor growth inhibition, with % tumor growth inhibitions (TGIs) ranging from 66-83% as compared to vehicle treated control animals. Once daily administration of compound (1) was as efficacious as twice daily treatments with either the 14+/7− or 21 day treatment schedule without dose dependency. Moreover, a shorter dosing duration (14+/7−) was as effective in inhibiting A549 tumor growth as dosing for a full 21 days.

To investigate the breadth of antitumor activity of compound (1), four additional efficacy studies were conducted in two colorectal cancer (Lovo and HCT116) and two non-small cell lung cancer (NSCLC) (Calu-6 and H460a) xenograft models. Although the parameters that might drive efficacy are unknown, the expression of Notch downstream targets Hes-1 and Hey-1 are thought to indicate an active Notch signaling pathway. Furthermore, Ras oncogene expression has been reported to play a role in Notch activation. Based on in-house gene expression profiling of Notch ligands, receptors, and downstream targets, the Lovo, HCT116, and Calu-6 tumor models were predicted to be sensitive to compound (1) mediated growth inhibition, whereas the H460a model was predicted to be insensitive. For example, the Lovo colorectal carcinoma cell line has similar gene expression as the A549 xenograft model already shown to be sensitive to compound (1) mediated tumor growth inhibition, with expression of the Notch ligands Jag 1 and DNER, Notch receptors 1, 2, and 3, and downstream targets Hes-1 and Hey-1. The NSCLC cell lines Calu-6 and H460a have similar ligand and receptor gene profiles with high expression of both Notch 1 and Notch 3. These two cell lines also have elevated expression of Hes-1, Hey-1 and NUMB. Moreover, all of these cell lines have mutant K-ras.

In the current study, compound (1) was administered orally for up to three weeks to mice bearing established subcutaneous (sc) Lovo, Calu-6, HCT116, or H460a tumors. Compound (1) was dosed at 3 mg/kg and 10 mg/kg daily (qd) for 21 days, or at 30 mg/kg and 60 mg/kg on an intermittent schedule (7 days on, 14 days off, and then 7 days on (7+/14−/7+)).

Materials and Methods

Animals

Female nude mice (10/group), obtained from Charles River Laboratories (Wilmington, Mass.) were used when they were approximately 13-14 weeks old and weighed approximately 23-25 grams. The health of all animals was determined daily by gross observation of experimental animals and by the analyses of blood samples of sentinel animals that were housed on the shared shelf racks. All animals were allowed to acclimate and recover from any shipping related stress for a minimum of 72 hours prior to experimental use. Autoclaved water and irradiated food [5058-ms Pico chow (mouse) Purina, Richmond, Ind.] were provided ad libitum, and the animals were maintained on a 12-hour light and dark cycle. Cages, bedding and water bottles were autoclaved before use and were changed weekly.

Tumors

Lovo human colorectal, Calu-6 NSCLC, and HCT116 colorectal cells were purchased from ATCC (Manassas, Va.). H460a NSCLC cells were a gift from Dr. Jack Roth, MD Anderson Medical Center, Houston, Tex. Lovo cells were cultured in F12K culture medium, Calu-6 and H460a were grown in Dulbecco's Modified Essential Medium (DMEM), and HCT116 cells were grown in McCoy's 5A medium. All culture media were supplemented with 10% (v/v) FBS and 1% (v/v) 200 nM L-glutamine. Mice were implanted with $5 \times 10^6$ Lovo, $3 \times 10^6$ Calu-6 or HCT116, or $1 \times 10^7$ H460a cells subcutaneously (sc) in a volume of 0.2 ml PBS per mouse in the right hind flank on Sep. 22, 2006, Sep. 22, 2006, Sep. 26, 2006, and Sep. 29, 2006 respectively.

Test Agent

Compound (1) was formulated as a suspension in 1.0% Klucel in water with 0.2% Tween-80 for oral (po) administration, as set out below.

Pharmaceutical Formulations

| Ingredients | Dose |
| --- | --- |
| Compound (1) | 7.5 mg/ml |
| Compound (1) | 3.73 mg/ml |
| Compound (1) | 1.25 mg/ml |
| Compound (1) | 0.375 mg/ml |

Formulated compound and vehicle were stored at 4° C. and prepared weekly. Compound (1) was mixed vigorously prior to administration.

Randomization

Mice implanted with Lovo and Calu-6 xenografts were randomized on day 19 post-implant, mice implanted with HCT116 xenografts were randomized on day 20, while mice implanted with H460a xenografts were randomized on day 12 post implant. All mice were randomized according to tumor volume, so that all groups had similar starting mean tumor volumes of approximately 100-180 mm³.

Study Design

The study design for all 4 in vivo studios in this report were identical. Dose groups are listed below.

Study Design

| Groups | Treatment | Dose | Schedule |
|---|---|---|---|
| 1 | Vehicle | — | qd × 21 days |
| 2 | Compound (1) | 3 mg/kg | qd × 21 days |
| 3 | Compound (1) | 10 mg/kg | qd × 21 days |
| 4 | Compound (1) | 30 mg/kg | qd × 7 days* |
| 5 | Compound (1) | 60 mg/kg | qd × 7 days* |

*received two rounds of 7 day treatment, except for the H460a efficacy study, which was discontinued early.

Treatment

Treatment for the Lovo and Calu-6 tumor studies began on Oct. 11, 2006 (day 19 post tumor cell implant), for the HCT116 study began on Oct. 16, 2006 (day 20 post tumor cell implant), and for the H460a study on Oct. 11, 2006 (12 days post tumor cell implant). Vehicle or compound (1) suspensions were dosed using a sterile 1 cc syringe and 18-gauge gavage needle (0.2 ml/animal) once daily (qd) for 21 days, or using an intermittent schedule (7 days on, 14 days off, and then 7 days on (7+/14−/7+)). For the Lovo and Calu-6 studies, 21 day dosing ended on day 40 post-tumor cell implant. For intermittent dosing, treatment ended on day 26, was reinitiated on day 40, and ended day 47. For the HCT116 study, 21 day dosing ended on day 42 post tumor cell implant. Intermittent dosing ended on day 27, was reinitiated on day 42, and ended day 49. For the H460a study, 21 day dosing ended early on day 27 post tumor cell implant, whereas for intermittent dosing, treatment ended day 19, and was not reinitiated (due to lack of efficacy).

Pathology/Necropsy

An end of the study, necropsy was performed for Eff #1137 (Lovo), Eff #1147 (HCT116), and Eff #1148 (H460a). Animals were injected with 1 mg BrdU (bromodeoxyuridine) in 1 ml of sterile water 2 hr prior to euthanization for assessment of tumor cell proliferation. Animals were euthanized by induction with $CO_2$ followed by cervical dislocation. Tumors from vehicle treated and selected compound (1) treated groups were collected and fixed in zinc-formalin overnight, processed, paraffin embedded, and sectioned for histopathology (Hematoxylin and Eosin (H & E) staining for morphological assessment, and BrdU staining) as set out below.

Necropsy/Pathology Summary

| Study No. | Groups | Dose/frequency | Animal No. |
|---|---|---|---|
| 1137 | Vehicle | qd × 21 days | 101-104 |
| 1137 | Compound (1) | 10 mg/kg qd × 21 days | 201-204 |
| 1137 | Compound (1) | 60 mg/kg × 7 days | 301-304 |
| 1147 | Vehicle | qd × 21 days | 101-104 |
| 1147 | Compound (1) | 10 mg/kg qd × 21 days | 201-204 |
| 1147 | Compound (1) | 60 mg/kg × 7 days | 301-304 |
| 1148 | Vehicle | qd × 21 days | 101-104 |
| 1148 | Compound (1) | 10 mg/kg qd × 21 days | 201-204 |

Monitoring

Tumor measurements and mouse weights were taken twice per week. All animals were individually followed throughout the experiment.

Calculations & Statistical Analysis

Weight loss was graphically represented as percent change in mean group body weight, using the formula:

$$((W-W_0)/W_0) \times 100$$

where W represents mean body weight of the treated group at a particular day, and $W_0$ represents mean body weight of the same treated group at initiation of treatment. Maximum weight loss was also represented using the above formula, and indicated the maximum percent body weight loss that was observed at any time during the entire experiment for a particular group.

Efficacy data was graphically represented as the mean tumor volume ±standard error of the mean (SEM). Tumor volumes of treated groups were presented as percentages of tumor volumes of the control groups (% T/C), using the formula:

$$100 \times ((T-T_0)/(C-C_0))$$

where T represented mean tumor volume of a treated group on a specific day during the experiment, $T_0$ represented mean tumor volume of the same treated group on the first day of treatment; C represented mean tumor volume of a control group on the specific day during the experiment, and $C_0$ represented mean tumor volume of the same treated group on the first day of treatment.

Tumor volume (in cubic millimeters) was calculated using the ellipsoid formula:

$$(D \times (d2))/2$$

where D represents the large diameter of the tumor, and d represents the small diameter.

In some cases, tumor regression and/or percent change in tumor volume was calculated using the formula:

$$((T-T_0)/T_0) \times 100$$

where T represents mean tumor volume of the treated group at a particular day, and $T_0$ represents mean tumor volume of the same treated group at initiation of treatment.

Statistical analysis was determined by the rank sum test and One Way Anova and a post-hoc Bonferroni t-test (SigmaStat, version 2.0, Jandel Scientific, San Francisco, Calif.). Differences between groups were considered to be significant when the probability value (p) was ≤0.05.

Results

The doses and regimens of compound (1) tested in the current set of studies were previously found to be well tolerated in nude mice. As expected, no body weight loss or other clinical signs of toxicity were noted in the current study.

Efficacy

In the current set of studies, compound (1) was tested at 3 and 10 mg/kg daily for 21 days, or at 30 and 60 mg/kg on an intermittent schedule (7 days on, 14 days off, and then 7 days on (7+/14−/7+)). When nude mice bearing Lovo colorectal xenografts were treated with compound (1) on either the 21 day or 7+/14−/7+ schedule, tumor growth was significantly inhibited, with maximal tumor growth inhibition identified on day 47, which was 7 days after the final day of treatment for the 21-day treated groups (21+/7−), or the end of treatment for the $2^{nd}$ round of 7 day treatment (7+/14−/7+). Doses of 3 and 10 mg/kg qd×21 days compound (1) resulted in 40% (p=0.136) and 83% (p≤0.001) TGI respectively as compared to vehicle treated controls, whereas doses of 30 and 60 mg/kg compound (1) dosed intermittently yielded 59% (p=0.021) and 85% (p=0.001) TGI.

Compared to the antitumor activity of compound (1) in the Lovo colorectal tumor model, tumor growth inhibition was attenuated in the Calu-6 NSCLC model. Maximal tumor growth inhibition was achieved on day 47, which was 7 days after the final day of treatment for the 21-day treated groups (21+/7−), and the end of treatment for the $2^{nd}$ round of 7 day treatment (7+/14−/7+). The greatest antitumor effect was found at the lowest dose of 3 mg/kg, which inhibited tumor growth by 59%, (p=0.011), while 10 mg/kg had a TGI of only 42% and was not statistically significant as compared to vehicle treated control mice (p=0.083). A dose of 30 mg/kg did not significantly inhibit Calu-6 tumor growth after two cycles of 7 day treatment (34% TGI, p=0.179), while doubling the dose to 60 mg/kg compound (1) resulted in 52% TGI (p=0.035).

Compound (1) mediated tumor growth inhibition in the HCT116 colorectal model was quite similar to that of the Lovo colorectal model, with significant antitumor activity identified with all doses and schedules. The maximal antitumor activity was noted on day 42 for the 21 day regimen (end of 21 day treatment), and day 53 for the 7+/14−/7+ regimen (3 days after end of second 7 day treatment). At the end of 21 days of consecutive daily treatments with 3 mg/kg compound (1), HCT116 colorectal tumors were growth inhibited by 85% (p≤0.001), and a dose of 10 mg/kg daily yielded 76% (p=0.003) TGI as compared to vehicle controls. Two rounds of 7 day treatment with 30 mg/kg and 60 mg/kg compound (1) produced TGIs of 63% (p=0.016) and 90% (p≤0.001), respectively.

The H460a NSCLC model proved completely resistant to compound (1) mediated tumor growth inhibition. Treatment of mice bearing H460 xenografts was terminated early (after only 2 weeks) due to lack of efficacy at all doses.

Similarly to a previous efficacy study in the A549 NSCLC xenograft model, in the current study it is of note that there was a general lack of dose response with respect to tumor growth inhibition with daily dosing. For instance, when compound (1) was dosed for 21 days at 3 or 10 mg/kg to HCT116 tumor-bearing mice, the resultant % TGIs were not dose proportional, with 85% and 76% TGI respectively. When the same doses of compound (1) were administered to Calu-6 tumor-bearing mice for 21 days, the % TGI for the higher dose was less compared to the lower dose (42% TGI vs. 59% TGI).

Disruption of Notch signaling through oral administration of the γ-secretase inhibitor, compound (1), to nude mice bearing established tumors resulted in antitumor efficacy. Earlier findings have shown that compound (1) was effective in prolonged and durable inhibition of A549 NSCLC tumors implanted in nude mice. Additional in vivo studies were initiated to investigate the breadth of antitumor efficacy of compound (1). The Lovo colorectal carcinoma, Calu-6 NSCLC, HCT116 colorectal carcinoma and H460a NSCLC were chosen to be tested in in vivo xenograft studies based on evidence of endogenous Notch signaling. Compound (1) was efficacious and significantly inhibited tumor growth without toxicity in three of the four tumor models.

In the current set of efficacy studies, two doses each of compound (1) were tested in two different regimens; 3 and 10 mg/kg qd for 21 days, or 30 and 60 mg/kg given intermittently (7+/14−7+). These doses and schedules were tested previously and found to be well tolerated in nude mice. Compound (1) demonstrated the greatest antitumor activity in the two colorectal models, Lovo and HCT116. After dosing for 21 days, doses of 3 and 10 mg/kg compound (1) resulted in 40% and 83% TGI respectively as compared to vehicle treated controls, whereas doses of 30 and 60 mg/kg compound (1) yielded 59% and 85% TGI. In the HCT116 model, the lowest dose of 3 mg/kg was even more active (TGI=85%), and a dose of 10 mg/kg was similarly efficacious, with 76% TGI as compared to vehicle treated controls. Two rounds of 7 day treatment with 30 mg/kg and 60 mg/kg compound (1) produced TGIs of 63% and 90% respectively.

Compound (1) was less effective against the two NSCLC xenograft models tested (Calu-6 and H460a). In the Calu-6 model, maximal growth inhibition (59% TGI as compared to vehicle) was achieved at the lowest dose of 3 mg/kg given daily for 21 days, whereas all other doses and regimens proved less effective. The H460a model was completely refractory to the antitumor effects of compound (1).

Although the data set thus far is small with only four tumor models tested in all, the observed antitumor responses in vivo appears to correlate with the cell lines Notch 1/Notch 3 expression ratios. Notch 3 has been shown to act as a negative regulator of intracellular Notch 1 (ICN) after processing and proteolytic cleavage by γ-secretase. Notch 3 competes with ICN after nuclear translocation and binding for transcription factors. In-house data revealed elevated expression of Notch 3 protein in H460a cells and reduced or low expression in the sensitive cell lines (i.e. Lovo, HCT116, and A549).

As noted in a previous in vivo study with compound (1), there was a general lack of dose proportionality observed here with respect to tumor growth inhibition when mice were dosed daily for 21 days. On the other hand, there did seem a dose response with higher doses given on the intermittent (7+/14−/7+) schedule. The perceived lack of a dose response cannot be fully explained by drug exposure. A comparison of plasma exposures in acute vs. chronically dosed mice with 10 mg/kg compound (1) demonstrated similar exposures, indicating there was not a loss of exposure over time that might explain the lack of a dose proportional antitumor response. Further, another pharmacokinetic study in nude mice revealed excellent dose proportionality with respect to plasma exposure up to a 30 mg/kg dose. Thus, the lack of dose proportional response in terms of TGI is not due to plasma exposure drug saturation. Again, these studies confirm that % TGI is not always proportional to exposure, and suggests a biological threshold effect.

Results from the in vivo studies described here demonstrate the breadth of antitumor activity of the γ-secretase inhibitor compound. Daily oral administration or intermittent (i.e. two cycles) dosing can effectively inhibit tumor growth without toxicity. Compound (1) is orally active in three out of four xenograft models. These data demonstrate that Notch inhibition through administration of the γ-secretase inhibitor, compound (1), may be an effective strategy for cancer treatment.

Conclusions

Compound (1) is a potent inhibitor of γ-secretase, which blocks activation of Notch signaling in tumor cells. In a previous study, administration of compound (1) orally to A549 tumor-bearing mice resulted in a sustained antitumor response. To further assess the breadth of antitumor activity of compound (1), four efficacy studies were conducted in the Lovo and HCT116 human colorectal, and Calu-6 and H460a NSCLC xenograft models. Two doses (3 and 10 mg/kg) were given daily for 21 days, while 30 and 60 mg/kg were given using an intermittent schedule (7 days on, 14 days off, and then 7 days on (7+/14−/7+)). Compound (1) demonstrated the greatest antitumor activity in the two colorectal models, Lovo and HCT116. After dosing for 21 days, a dose of 10 mg/kg compound (1) resulted in 83% tumor growth inhibition (TGI) as compared to vehicle treated controls, whereas doses of 30 and 60 mg/kg of compound (1) yielded 59% and 85% TGI. In the HCT116 model, a dose as low as 3 mg/kg was efficacious, with 85% TGI as compared to vehicle controls, and a dose of 10 mg/kg was similarly efficacious. Two rounds of 7 day treatment with 30 mg/kg and 60 mg/kg compound (1) produced TGIs of 63% and 90%, respectively. Compound (1) was less effective against the two NSCLC xenograft models tested, Calu-6 and H460a. In the Calu-6 model, significant growth inhibition (59% TGI as compared to vehicle) was achieved only at the lowest dose of 3 mg/kg given daily for 21 days, whereas all other doses and regimens proved less effective. The H460a model was completely refractory to the antitumor effects of compound (1). The observed pattern of antitumor activity seems to correlate with the cell lines' Notch1/Notch3 expression ratio, however the data set is small and the factors driving efficacy are still poorly understood. These data demonstrate that Notch inhibition through administration of the γ-secretase inhibitor, compound (1), may be an effective strategy for cancer treatment.

Example 2

Cellular Activity of Compound (1) in A549 NSCLC Tumor Cells

Compound (1) $IC_{50}$ in cellular and cell-free assays is in the low nanomolar range with a >2 log unit selectivity observed with respect to 75 other binding sites of various types (receptors, ion channels, enzymes). The growth inhibitory activity of compound (1) is complex. Compound (1) does not block tumor cell proliferation nor induce apoptosis but instead produces a less transformed more flattened slower growing phenotype. This mechanism is consistent with Notch inhibition and precludes collecting standard EC50 values. Compound (1) reduces Notch processing as measured by the reduction in ICN expression by Western blot. This leads to reduced expression of the transcriptional target gene product, Hes1, also measured by Western blot.

During development and tissue remodeling, pluripotent stem cells serve as the source for differentiating cells to give rise to non-proliferating specialized cell types. A link between the characteristics of these stem cells and the rapid uncontrolled proliferation of tumors is becoming clear. One of the major developmental signaling axes is the Notch pathway. Notch signaling regulates cell-fate by mediating the differentiation of progenitor cells during development and self-renewal of adult pluripotent stem cells. Notch functions to maintain progenitor cells in a pluripotent rapidly proliferating state. Notch gene amplification, chromosomal translocation, or mutations lead to elevated Notch signaling, thereby imparting a tumor growth advantage by keeping tumor cells in a stem cell-like proliferative state.

Intramembrane processing is an emerging theme for membrane receptor activation and signaling. γ-secretase is a key enzyme in the intramembrane proteolytic processing of several signaling receptors, including Notch (other examples of proteins processed by γ-secretase are amyloid precursor protein [APP], CD44 stem cell marker, and HER4 [ErbB4]). The γ-secretase processing of Notch produces the active form called ICN. This protein translocates to the nucleus and forms part of a large transcription complex involving the CSL transcriptional regulator directly altering the expression of key proliferation- and differentiation-specific genes. Blocking Notch signaling via γ-secretase inhibition produces a slower growing, less transformed phenotype in human cancer cells in vivo. This type of novel treatment approach holds the potential to make cancer a more manageable disease without the strong side-effects of traditional cytotoxic drugs.

Materials and Methods

Cell Lines and Culture

The A549 cell line was obtained from the American Tissue Culture Collection (ATCC), Manassas, Va. and maintained in Ham's media supplemented with 10% heat-inactivated Fetal Bovine Serum (HI-FBS; GIBCO/BRL, Gaithersburg, Md.) and 2 mM L-glutamine (GIBCO/BRL). $1 \times 10^6$ A549 cells were seeded in 10 $cm^3$ plates for FACS analysis and $3 \times 10^5$ cells per well were seeded in 6-well plate for Western blot analysis. Cells were allowed to attach for 24 hours and then treated with compound (1) compound at the following concentrations: 0.1, 0.25, 0.5, 1, 2.5 and 5 µM. Cells were incubated for either 72 or 120 hours and collected for FACS analysis.

Test Articles

The test compound (1) was dissolved at 10 mM in 100% dimethyl sulfoxide (DMSO) (Sigma) and stored at −20° C. in a glass vial.

5-Point Dosing and Western Blot Analysis

A549 cells were collected by washing plates with cold PBS and adding sample buffer (1:1 water: 2× Tris-Glycine SDS Sample Buffer (Invitrogen, Carlsbad, Calif.) containing 5% 2-β mercaptoethanol) directly onto plates. The volume of lysis buffer used was approximately 100 µl per $1 \times 10^5$ cells. Proteins were denatured by boiling for 5 minutes, resolved by SDS-polyacrylamide gel electrophoresis using a 4-20% Tris-glycine gel (Invitrogen) and electroblotted onto a 0.45 µm nitrocellulose membrane (Invitrogen). Membranes were blocked 1 hr at room temperature in blocking buffer (5% milk in PBS/0.1% Tween 20) followed by incubation with the primary antibody at 4° C. overnight. Membranes were washed and incubated with the secondary antibody for 30 minutes at room temperature Immunodetection was carried out using enhanced chemoluminescence (ECL Plus, Amersham Pharmacia Biotech, Piscataway, N.J.). For Western blotting, total ICN was detected using the cleaved Notch-1 (val1744) antibody from Cell Signaling (#2421) at a dilution of 1:1000, Hes1 was detected using the Hes1 antibody from US Biological (#H2034-35) at a dilution of 1:1000, and actin was detected using the actin antibody from Sigma (#5316) at a dilution of 1:10,000.

Cell Cycle Analysis

Cells were incubated with compound (1) for 72 or 120 hours, harvested by scraping, washed twice in phosphate-buffered saline (PBS), spun down at $1.5 \times 10^3$ rpm, and fixed at −20° C. overnight with 70% ethanol. Cells were then analyzed using MPM2-FITC and propidium iodide (PI) double staining (Becton Dickinson, San Jose, Calif.). Briefly, cells were washed twice with cold PBS containing 0.05% Tween-20 (PBST), incubated for 2 hours with anti-Phospho Ser/Thr MPM2 antibody (#05-368, Upstate/Millipore, Bullerica, Mass.), washed with PBST again, incubated in the dark with secondary IgG-FITC antibody (#AP308F, Chemicon, Temecula, Calif.), washed with PBST and incubated with PI/RNase solution (Becton Dickinson, San Jose, Calif.) for additional 30 min at 37° C.

Samples were analyzed on a FACScan flow cytometer (Becton Dickinson, San Jose, Calif.) equipped with a 488 nm argon ion laser. Green fluorescein isothiocyanate (FITC) fluorescence was collected with a 530/30 nm bandpass filter using logarithmic amplification and orange emission from propidium iodide (PI) was filtered through a 585/42 nm bandpass filter using linear amplification. A minimum of 20,000 events was collected on each sample. Cell cycle analysis of DNA histograms was performed with FlowJo software (Tree Star Inc., Ashland, Oreg.).

Western Blot Analysis of Notch Processing

The formation of the ICN protein following Notch receptor cleavage by γ-secretase is a critical step in Notch signaling. ICN moves to the nucleus becoming part of a larger transcriptional complex regulating the transcription of various target genes including Hes1. The reduction of ICN expression and the Notch target gene product, Hes1, in tumor cell lines was monitored by Western blot. Compound (1) suppresses the production of ICN inducing a flattened and less transformed tumor cell phenotype in tissue culture after five days of treatment in the human NSCLC A549 cells. The morphology is similar to the nontransformed primary bronchial epithelia cells grown in tissue culture. A comparative was obtained from the Clonetics website for visual comparison. This data is consistent with inhibiting γ-secretase in tumor cells. The appearance of an apoptotic phenotype following compound treatment was not observed.

Cell Cycle Analysis

FACS analysis was utilized to gain an understanding of the cell cycle inhibitory effects following compound (1) treatment. A549 cells were treated for 72 and 120 hours with increasing concentrations of compound (1). FACS analysis shows little effect on cell cycle progression with a modest cell cycle slowing with 5 µM at 72 and 120 hours, as set out below.

Quantitation of FACS Analysis

| Compound (1), µM | Time, hrs | subG1, % | G1, % | G2/M, % |
| --- | --- | --- | --- | --- |
| 0 | 72 | 5.2 | 60.1 | 23.5 |
| 0.10 | | 6.5 | 63.1 | 23.3 |
| 0.25 | | 5.9 | 64.8 | 20.3 |
| 0.50 | | 4.3 | 66.6 | 19.4 |
| 1.0 | | 6.6 | 64 | 21.5 |
| 5.0 | | 8.4 | 64.9 | 20 |
| 0 | 120 | 7.2 | 58.2 | 59 |
| 0.10 | | 6.8 | 59.0 | 24.1 |
| 0.25 | | 6.7 | 61.1 | 23.8 |
| 0.50 | | 9.6 | 58.6 | 23.3 |
| 1.0 | | 8.0 | 60.9 | 19.8 |
| 5.0 | | 13.7 | 58.7 | 18.3 |

Conclusion

Compound (1) does not block tumor cell proliferation nor induce apoptosis but instead produces a less transformed more flattened and slower growing phenotype. This mechanism is consistent with Notch inhibition. Compound (1) reduces Notch processing as measured by the reduction in ICN expression by Western blot. This leads to reduced expression of the transcriptional target gene product, Hes1, also measured by Western blot.

Example 3

A549 Xenograft Western Blot Analysis Following Compound (1) Dosing

Compound (1) is a potent and selective inhibitor of γ-secretase producing inhibitory activity of Notch signaling in tumor cells (1). Compound (1) $IC_{50}$ in cellular and cell-free assays is in the low nanomolar range with a >2 log unit selectivity observed with respect to 75 other binding sites of various types (receptors, ion channels, enzymes). The growth inhibitory activity of compound (1) is complex. Compound (1) does not block tumor cell proliferation nor induce apoptosis but instead produces a less transformed more flattened and slower growing phenotype. This mechanism is consistent with Notch inhibition. Compound (1) treated tumors have reduced level of the extracellular matrix proteins collagen type 5 and elevated levels of MFAP5. In addition, Notch processing is inhibited in the tumor cells as measured by the loss of ICN and Notch-1 receptor expression. When mice bearing A549 xenografts were dosed up to 60 mg/kg with compound (1) per day, ICN and Notch-1 was variable. This was possible due to a loss of exposure following repeated dosing over the course of the efficacy study or poor compound distribution within the tumor During development and tissue remodeling, pluripotent stem cells serve as the source for differentiating cells to give rise to non-proliferating specialized cell types. A link between the characteristics of these stem cells and the rapid uncontrolled proliferation of tumors is becoming clear. One of the major developmental signaling axes is the Notch pathway. Notch signaling regulates cell-fate by mediating the differentiation of progenitor cells during development and self-renewal of adult pluripotent stem cells. Notch functions to maintain progenitor cells in a pluripotent rapidly proliferating state. Notch gene amplification, chromosomal translocation, or mutations lead to elevated Notch signaling, thereby imparting a tumor growth advantage by keeping tumor cells in a stem cell-like proliferative state.

Intramembrane processing is an emerging theme for membrane receptor activation and signaling. -secretase is a key enzyme in the intramembrane proteolytic processing of several signaling receptors, including Notch (other examples of proteins processed by -secretase are amyloid precursor protein [APP], CD44 stem cell marker, and HER4 [ErbB4]). The -secretase processing of Notch produces the active form called ICN. This protein translocates to the nucleus and forms part of a large transcription complex involving the CSL transcriptional regulator directly altering the expression of key proliferation- and differentiation-specific genes. Blocking Notch signaling via -secretase inhibition produces a slower growing, less transformed phenotype in human cancer cells in vivo. This type of novel treatment approach holds the potential to make cancer a more manageable disease without the strong side-effects of traditional cytotoxic drugs.

Materials and Method

Test Articles

The test compound (1) was dissolved at 10 mM in 100% dimethyl sulfoxide (DMSO) (Sigma) and stored at −20° C. in a glass vial.

Tumor Harvest and Western Blot Analysis

A549 tumor bearing nude mice were dosed on a daily oral schedule at the indicated doses for 21 days. Three A549 tumors from each group were collected at the time of necropsy and flash frozen. Protein extracts were prepared by adding sample buffer (1:1 water: 2× Tris-Glycine SDS Sample Buffer (Invitrogen, Carlsbad, Calif.) containing 5% 2-β mercaptoethanol) directly onto tumors and disrupted with the aid of an eppendorf pestle. The volume of lysis buffer used was approximately 100 µl per $1 \times 10^6$ cells. Proteins were denatured by boiling for 5 minutes, resolved by SDS-polyacrylamide gel electrophoresis using a 4-20% Tris-glycine gel (Invitrogen) and electroblotted onto a 0.45 µm nitrocellulose membrane (Invitrogen). Membranes were blocked 1 hr at room temperature in blocking buffer (5% milk in PBS/0.1% Tween 20) followed by incubation with the primary antibody at 4° C. overnight. Membranes were washed and incubated with the secondary antibody for 30 minutes at room temperature. Immunodetection was carried out using enhanced chemoluminescence (ECL Plus, Amersham Pharmacia Biotech, Piscataway, N.J.). For Western blotting, total ICN was detected using the cleaved Notch 1 (val1744) antibody from Cell Signaling (#2421) at a dilution of 1:1000, total Notch-1 was detected using the Notch-1 C-20 antibody from Santa Cruz Biotechnology (#SC-6014) at a dilution of 1:1000, Hes1 was detected using the Hes1 antibody from US Biological (#H2034-35) at a dilution of 1:1000, actin was detected using the actin antibody from Sigma (#5316) at a dilution of 1:10, 000, Collagen type V was detected using the H-200 antibody from Santa Cruz biotechnology (#20648) at a dilution of 1:1000, and MFAP5 was detected using the MFAP5 antibody from Abnova (#H00008076-A01) at a dilution of 1:1000.

Xenograft Western Blot Analysis

Microarray analysis of -secretase inhibitor treated A549 xenograft tumors revealed RNA expression changes consistent with the extracellular matrix alteration. Compound (1) treated tumors treated were prepared for Western blot analysis. Collagen type V expression was significantly reduced while MFAP5 protein expression was elevated. Notch-1 protein levels and the expression of the ICN were reduced in all animal groups except for the highest dose group. Collagen type V and MFAP5 are structural proteins that make up the extracellular matrix. Collagen type V expression is often reduced and MFAP5 expression is often elevated in more differentiated tissues. This data is consistent with the working hypothesis that Notch-1 inhibition in A549 tumor cells leads to a more differentiated phenotype.

Conclusion

Compound (1) treated tumors have reduced levels of the extracellular matrix protein collagen type 5 and elevated levels of MFAP5. In addition, Notch processing is inhibited in the tumor cells as measured by the loss of ICN and Notch-1 receptor expression. When mice bearing A549 xenografts were dosed up to 60 mg/kg with compound (1) per day, ICN and Notch-1 was variable. This was possible due to a loss of exposure following repeated dosing over the course of the efficacy study or poor compound distribution within the tumor.

Example 4

Loss of Soft Agar Growth Potential in MDA-MB-468 Breast Tumor Cells after Dosing with Compound (1)

Compound (1) is a potent and selective inhibitor of -secretase producing inhibitory activity of Notch signaling in tumor cells. Compound (1) $IC_{50}$ in cellular and cell-free assays is in the low nanomolar range with a >2 log unit selectivity observed with respect to 75 other binding sites of various types (receptors, ion channels, enzymes). The growth inhibitory activity of compound (1) is complex. Compound (1) does not block tumor cell proliferation nor induce apoptosis but instead produces a less transformed more flattened and slower growing phenotype. This mechanism is consistent with Notch inhibition and precludes collecting standard $EC_{50}$ values. Compound (1) reduces the size of MDA-MB-468 colonies in soft agar.

During development and tissue remodeling, pluripotent stem cells serve as the source for differentiating cells to give rise to non-proliferating specialized cell types. A link between the characteristics of these stem cells and the rapid uncontrolled proliferation of tumors is becoming clear. One of the major developmental signaling axes is the Notch pathway. Notch signaling regulates cell-fate by mediating the differentiation of progenitor cells during development and self-renewal of adult pluripotent stem cells. Notch functions to maintain progenitor cells in a pluripotent rapidly proliferating state. Notch gene amplification, chromosomal translocation, or mutations lead to elevated Notch signaling, thereby imparting a tumor growth advantage by keeping tumor cells in a stem cell-like proliferative state.

Intramembrane processing is an emerging theme for membrane receptor activation and signaling. -secretase is a key enzyme in the intramembrane proteolytic processing of several signaling receptors, including Notch (other examples of proteins processed by secretase are amyloid precursor protein [APP], CD44 stem cell marker, and HER4 [ErbB4]). The -secretase processing of Notch produces the active form called ICN. This protein translocates to the nucleus and forms part of a large transcription complex involving the CSL transcriptional regulator directly altering the expression of key proliferation- and differentiation-specific genes. Blocking Notch signaling via -secretase inhibition produces a slower growing, less transformed phenotype in human cancer cells in vivo. This type of novel treatment approach holds the potential to make cancer a more manageable disease without the strong side-effects of traditional cytotoxic drugs.

Materials and Methods

Cell Lines and Culture

The MDA-MB-468 cell line was obtained from the American Tissue Culture Collection (ATCC), Manassas, Va. and maintained in RPMI media supplemented with 10% heat-inactivated Fetal Bovine Serum (HI-FBS; GIBCO/BRL, Gaithersburg, Md.) and 2 mM L-glutamine (GIBCO/BRL).

Test Articles

The test compound (1) was dissolved at 10 mM in 100% dimethyl sulfoxide (DMSO) (Sigma) and stored at −20° C. in a glass vial.

Soft Agar Colony Forming Assay

For anchorage-independent growth assays, a bottom layer of 2 ml of cell type-specific complete medium (RPMI media supplemented with 20% fetal bovine serum (FBS), 1% penicillin/streptomycin, 1% sodium pyruvate, 1% HEPES) containing 0.5% low melting temperature SeaPlaque agarose (#50100, Cambrex, Rockland, Me.) was poured into each well of 6-well plate. After agar medium solidified at room temperature, $3 \times 10^3$ cells/well were added in 0.5 ml of complete culture medium as described above, containing 0.3% SeaPlaque agarose. The next day 1 ml of media containing either 0, 100, or 250 nM of Compound (1) was added to the cells. Cells were incubated for 4 weeks to allow colonies to form, the media containing compound was replaced twice a week.

Soft Agar Growth

Compound (1) is a potent and selective inhibitor of -secretase producing inhibitory activity of Notch signaling in tumor cells. The growth inhibitory activity of compound (1) is complex. Compound (1) does not block tumor cell proliferation nor induce apoptosis but produces a less transformed and more flattened slower growing phenotype. The ability to form colonies in soft agar represents a critical event in tumor cell progression. Nontransformed cells and poorly tumorigenic cells fail to grow when plated in soft agar. In contrast, highly tumorigenic cells grow rapidly under soft agar conditions producing large colonies. The effect of compound (1) on the transformed phenotype was evaluated in the human breast cancer cell line MDA-MB-468 by measuring growth potential in soft agar. Compound (1) reduced colony growth in a dose-dependent manner (250 nM>100 nM>control).

Conclusions

Compound (1) does not block tumor cell proliferation but reduces the size of MDA-MB-468 colonies in soft agar. This is consistent with the induction of a less transformed phenotype by compound (1) in MDA-MB-468 breast tumor cells.

Example 5

Tolerability and Efficacy of Once or Twice Daily Oral Administration of γ-Secretase Inhibitor Compound (1) in Nude Mice Bearing A549 Non-Small Cell Lung Carcinoma Xenografts Compound (1) is a potent and highly selective inhibitor of γ secretase originally for the treatment of Alzheimer's disease. In vitro, compound (1) inhibits Notch activation and processing at nanomolar concentrations, and addition of compound (1) to tumor cells in culture induces a less transformed phenotype and blocks growth in soft agar. In vivo, compound (1) has good oral bioavailability, and favorable pharmacokinetic profiles in rodents, dog and humans. In the current study, nude mice bearing A549 non-small cell lung carcinoma (NSCLC) xenografts were dosed orally qd or bid either 7, 14, or 21 days out of a 21 day treatment cycle with compound (1). For bid dosing, maximum tolerated doses (MTDs) of 60 mg/kg for 7 days, 30 mg/kg for 14 days, and 10 mg/kg for 21 days were identified. For qd dosing, maximum tolerated doses of 60 mg/kg for 14 days or 30 mg/kg for 21 days were noted. When 60 mg/kg compound (1) was administered for only 7 days out of 21 day cycle (7+/14−), tumor regression was initially observed, and after 14 days without treatment, % tumor growth inhibition (TGI) was still 91% as compared to vehicle treated control animals. Additionally, lower doses of compound (1) (3 mg/kg, 10 mg/kg and 30 mg/kg) given once or twice daily for 14 (14+/7−) or 21 days resulted in significant and sustained tumor growth inhibition at the end of the 21 days cycle, with % TGIs ranging from 66-83%. Once daily administration of compound (1) was as efficacious as twice daily treatments with either the 14+/7− or 21 day treatment schedule with dose dependency. Moreover, shorter dosing durations (7+/14− or 14+/7−) were as effective in inhibiting A549 tumor growth as dosing for a full 21 days. This data supports the idea that Notch inhibition through administration of the γ secretase inhibitor compound (1) could be an effective clinical therapy for the treatment of cancer.

The Notch signaling pathway is involved in determining cell fate during development through regulation of differentiation, proliferation, and apoptosis in progenitor and pluripotent stem cells. Dysregulation of Notch signaling components due to gene amplification, chromosomal translocation, or mutations has been implicated in many types of malignancy including leukemia, medullo- and glioblastoma, breast carcinoma, head and neck cancer, and pancreatic carcinoma. For example, Notch plays a role in determining the lineage of cells in the hematopoietic system, and activating Notch-1 mutations have been shown responsible for about half of all T-cell ALLs (acute lymphoblastic leukemia). The Notch signaling pathway is comprised of Notch receptors (Notch receptors 1-4), whereupon binding of ligands (Delta-like-1, -3, -4, Jagged-1 and -2) and activation through proteolytic cleavage, translocate to the nucleus where they act as transcriptional activators for target genes.

γ-secretase is one of two key enzymes responsible for the cleavage and activation of Notch receptors, and has been proposed as a target for cancer treatment. Enzymatic cleavage of intracellular Notch (ICN) by γ-secretase allows ICN to translocate to the nucleus leading to transcription of downstream oncogenic targets including Hes, Hes related bHLH repressors, Hey, HERP, cell cycle regulators (p21, Cyclin A, cyclin D1), SKP2, transcription factors of NF-κB, AKT, PI-3K, erbB2, β-catenin and regulators of the apoptotic process. Ras oncogenes can activate wild-type Notch signaling, an apparent requirement for Ras-mediated transformation to malignancy. Recent evidence indicates that Notch signaling from tumor cells can trigger Notch activation of neighboring endothelial cells consequently promoting tumorigenesis and angiogenesis. Thus γ-secretase inhibitors targeting Notch activity could have pleiotropic effects in different cancer types.

In addition to processing Notch, γ-secretase is also responsible for processing β-amyloid precursor peptide (APP), a target in the treatment of Alzheimer's disease. Small molecules targeting γ-secretase have been shown to be capable of some degree of selectivity for blocking the processing of APP vs. Notch. The current clinically lead, compound (1) was developed for Alzheimer's, but lacked sufficient specificity for inhibition of APP Vs γ-secretase. The consequences of targeting Notch in normal cells were deemed unsuitable for the Alzheimer's indication, but acceptable for Oncology. For example, toxicological studies in Fischer rats dosed with a γ-secretase inhibitor revealed Notch pathway activation blockade that resulted in increased size and number of mucosecreting goblet cells.

Compound (1) is a highly selective and potent inhibitor of γ-secretase ($IC_{50}$=4 nM). Recognizing the mounting data linking dysregulation of the Notch signaling pathway and cancer, a cross-therapeutic strategy was employed to utilize γ-secretase inhibitors as cancer therapeutics. Compound (1) inhibits human Abeta protein production ($IC_{50}$=4-14 nM), and Notch activity/processing in a cellular reporter assay ($IC_{50}$=5 nM) in the nanomolar range. Compound (1) has favorable pharmacokinetic profiles in mouse, with moderate to high oral bioavailability.

In the current study, compound (1) was evaluated for its antitumor activity against the A549 NSCLC human xenograft model in nude mice. A549 cells appear to have a functional Notch signaling pathway since receptors, ligands, and downstream effectors such as Hes-1 and Hey-1 are expressed (as assessed by PCR-based gene expression profiling). A549 cells have at least one identifiable defect in the Notch pathway; the negative regulator Numb is expressed only at low levels. In vitro, nM concentrations of compound (1) induce a less transformed phenotype in A549 cells and loss of growth in soft agar with MDA-MB-468 breast tumor cells, which is consistent with mechanistic inhibition of Notch activation. To test the antitumor effect of compound (1) in vivo, in the present study compound (1) was administered once (qd) or twice (bid) daily for either 7, 14 or 21 days out of a 21 day schedule to female athymic nu/nu (nude) mice bearing A549 xenografts.

Materials and Methods

Animals

Female nude mice (10/group), obtained from Charles River Laboratories (Wilmington, Mass.) were used when they were approximately 13-14 weeks old and weighed approximately 23-25 grams. The health of all animals was determined daily by gross observation of experimental animals and by the analyses of blood samples of sentinel animals that were housed on the shared shelf racks. All animals were allowed to acclimate and recover from any shipping related stress for a minimum of 72 hours prior to experimental use. Autoclaved water and irradiated food [5058-ms Pico chow (mouse) Purina, Richmond, Ind.] were provided ad libitum, and the animals were maintained on a 12 hour light and dark cycle. Cages, bedding and water bottles were autoclaved before use and were changed weekly.

Tumors

A549 human NSCLC cells were purchased from ATCC (Manassas, Va.) and cultured in RPMI 1640 culture medium with 10% (v/v) FBS. Cells were grown and harvested by members of the Oncology In Vivo Section (OIVS). Each mouse received $7.5 \times 10^6$ cells in 0.2 ml PBS (Phosphate Buffered Saline) implanted subcutaneously in the right hind flank by members of OIVS on Aug. 17, 2006.

Test Agents

Compound (1) was formulated as a suspension in 1.0% Klucel in water with 0.2% Tween-80 for oral (po) administration. Compound (1) was mixed vigorously prior to withdrawal and administration. Formulated compound and vehicle were prepared weekly and stored at 4° C., as set out below.

Pharmaceutical Formulations

| Ingredients | Dose |
| --- | --- |
| Compound (1) | 0.375 mg/ml |
| Compound (1) | 1.25 mg/ml |
| Compound (1) | 3.75 mg/ml |
| Compound (1) | 11.25 mg/ml |

Randomization

On day 25, post-tumor implant animals were randomized according to tumor volume, so that all groups had similar starting mean tumor volumes of approximately 100-150 mm$^3$.

Study Design

Dose groups are set out below.

Study Design

Groups Dosed for 7 and 14 Days

| Groups | Treatment | Dose | Schedule |
| --- | --- | --- | --- |
| 1 | Vehicle | — | bid × 14 days |
| 2 | Compound (1) | 3 mg/kg | qd × 14 days |
| 3 | Compound (1) | 10 mg/kg | qd × 14 days |
| 4 | Compound (1) | 30 mg/kg | qd × 14 days |
| 5 | Compound (1) | 60 mg/kg | qd × 14 days |
| 6 | Compound (1) | 3 mg/kg | bid × 14 days |
| 7 | Compound (1) | 10 mg/kg | bid × 14 days |
| 8 | Compound (1) | 30 mg/kg | bid × 14 days |
| 9 | Compound (1) | 60 mg/kg | bid × 14 days |
| 10 | RO3929097 | 60 mg/kg | bid × 7 days |

Groups Dosed for 21 Days

| Groups | Treatment | Dose | Schedule |
| --- | --- | --- | --- |
| 11 | Vehicle | — | bid × 21 days |
| 12 | Compound (1) | 3 mg/kg | qd × 21 days |
| 13 | Compound (1) | 10 mg/kg | qd × 21 days |
| 14 | Compound (1) | 30 mg/kg | qd × 21 days |
| 15 | Compound (1) | 60 mg/kg | qd × 21 days |
| 16 | Compound (1) | 3 mg/kg | bid × 21 days |
| 17 | Compound (1) | 10 mg/kg | bid × 21 days |
| 18 | Compound (1) | 30 mg/kg | bid × 21 days |
| 19 | Compound (1) | 60 mg/kg | bid × 21 days |

Treatment

Treatment began on Sep. 12, 2006 (day 26 post tumor cell implant). Compound (1) and vehicle were dosed as a suspension using a sterile 1 cc syringe and 18-gauge gavage needle (0.2 ml/animal) once (qd) or twice per day (bid) 8 hours apart for either 7, 14 or 21 days out of a 21 day schedule. For animals dosed for 7 days (7+/14−), treatment ended on Sep. 19, 2006 (day 33 post tumor cell implant). These mice were re-treated on day 67 with the same dose of compound (1) for another 7 days until day 74. For animals dose for 14 days (14+/7−) treatment ended on Sep. 26, 2006 (day 40 post tumor cell implant), and for animals dosed for 21 days, treatment ended on Oct. 3, 2006 (day 47 post tumor cell implant).

Pathology and Necropsy

Animals were injected with 1 mg BrdU (bromodeoxyuridine) in 1 ml of sterile water 2 hr prior to euthanization for assessment of tumor cell proliferation. Animals were euthanized by induction with $CO_2$ followed by cervical dislocation. Tumors from vehicle treated and selected compound (1) treated groups were collected and fixed in zinc-formalin overnight, processed, paraffin embedded, and sectioned for histopathology (Hematoxylin and Eosin (H & E) staining for morphological assessment, and BrdU staining). Spleens and portions of the gastrointestinal tract were collected and formalin-fixed, processed, paraffin embedded, sectioned, and stained with H & E for assessment of marginal zone B-cell depletion, and goblet cell formation respectively, as these are two known target-related effects of γ-secretase inhibitors. The results are set out below.

Necropsy/Pathology Summary

| Groups | Dose/frequency/route | Animal number |
| --- | --- | --- |
| 1. Vehicle | qd × 21 days, po | 101-104 |
| 2. Compound (1) | 3 mg/kg, qd × 21 days, po | 201-204 |
| 3. Compound (1) | 10 mg/kg, qd × 21 days, po | 301-304 |

Monitoring

Tumor measurements and mouse weights were taken twice per week. All animals were individually followed throughout the experiment.

Calculations & Statistical Analysis

Weight loss was graphically represented as percent change in mean group body weight, using the formula: $((W-W_0)/W_0) \times 100$, where 'W' represents mean body weight of the treated group at a particular day, and '$W_0$' represents mean body weight of the same treated group at initiation of treatment. Maximum weight loss was also represented using the above formula, and indicated the maximum percent body weight loss that was observed at any time during the entire experiment for a particular group. Toxicity is defined as ≥20% of mice in a given group demonstrating ≥20% body weight loss and/or mortality.

Efficacy data was graphically represented as the mean tumor volume+standard error of the mean (SEM). Tumor volumes of treated groups were presented as percentages of tumor volumes of the control groups (% T/C), using the formula: $100 \times ((T-T_0)/(C-C_0))$, where T represented mean tumor volume of a treated group on a specific day during the experiment, $T_0$ represented mean tumor volume of the same treated group on the first day of treatment; C represented mean tumor volume of a control group on the specific day during the experiment, and $C_0$ represented mean tumor volume of the same treated group on the first day of treatment. Tumor volume (in cubic millimeters) was calculated using the ellipsoid formula: $(D \times (d2))/2$ where 'D' represents the large diameter of the tumor, and 'd' represents the small diameter. In some cases, tumor regression and/or percent change in tumor volume was calculated using the formula: $((T-T_0)/T_0) \times 100$ where 'T' represents mean tumor volume of the treated group at a particular day, and '$T_0$' represents mean tumor volume of the same treated group at initiation of treatment. Statistical analysis was determined by the rank sum test and One Way Anova and a post-hoc Bonferroni t-test (SigmaStat, version 2.0, Jandel Scientific, San Francisco, Calif.).

Differences between groups were considered to be significant when the probability value (p) was ≤0.05.

Drug Exposure

To assess chronic drug exposure, blood samples were collected from 2 mice per time point from the 10 mg/kg compound (1) group (qd×21 days) at 0.5, 1, 2, 4, 8, and 24 h after the last dose. To assess acute drug exposure, a naive group of nude mice was administered a single dose of 10 mg/kg compound (1) on the last study day. Plasma samples were prepared and analyzed for compound (1) by LC/MS/MS.

Mean plasma concentrations were calculated from 2 animals/group/time point. Plasma samples with concentration below the limit of quantification (<12.5 ng/ml) were set to zero. The pharmacokinetic parameters were estimated from the mean plasma concentration data. Sampling times were reported as nominal time. The pharmacokinetic parameters reported are the maximum plasma concentration (Cmax), the area under the plasma concentration-time curve from zero to 8 hr ($AUC_{0-8\ hr}$), and dose normalized AUC ($AUC_{0-8\ hr}$/Dose). The Cmax values were taken directly from the plasma concentration-time profiles at the first time point without any extrapolation. The AUC was calculated using the linear trapezoidal rule.

In mice dosed chronically, a dose of 10 mg/kg produced a Cmax of 708 ng*Hours/ml and an $AUC_{0-8\ hr}$ of 923 ng*Hours/ml. A single dose in naïve mice provided similar exposure, with a Cmax and $AUC_{0-8\ hr}$ of 559 ng*Hours/ml and 1279 ng*Hours/ml respectively indicating there was neither drug accumulation nor declining exposure upon chronic dosing. The results are set out below.

Drug Exposure Summary

Mean Plasma Exposure with 10 mg/kg Dose

| Parameter (ng * Hours/ml) | Day 1 | Day 21 |
| --- | --- | --- |
| $AUC_{0-8\ hr}$ | 1279 | 923 |
| Cmax | 559 | 709 |

Results

Toxicity

In a previous maximum tolerated dose (MTD) study, 90 mg/kg compound (1) dosed bid to naive nude mice for 14 days was toxic and resulted in significant body weight loss, whereas 90 mg/kg dosed once daily was tolerated. In the current study, 60 mg/kg compound (1) dosed bid was not tolerated beyond 7 days, and qd was not tolerated beyond 14 days. When animals were dosed with 60 mg/kg bid for 21 or 14 days, seven and four mice died from each treatment group, respectively, with most animals exhibiting preceding body weight loss prior to death. When animals were dosed qd for 21 days, three mice died. A dose of 60 mg/kg qd for 14 or bid for 7 days was well tolerated, with no appreciable weight loss or other clinical signs of toxicity.

A dose of 30 mg/kg was tolerated qd for 21 days, however a dose of 30 mg/kg bid for 21 days was toxic, with two animal deaths. A dose of 30 mg/kg dosed either qd or bid was well tolerated for 14 days with no appreciable weight loss or other clinical signs of toxicity. Doses lower than 30 mg/kg (i.e. 10 mg/kg or 3 mg/kg) were well tolerated with all dosing schedules and no gross clinical signs of toxicity were observed.

Antitumor Efficacy

Once or twice daily oral administration of compound (1) to nude mice bearing A549 NSCLC xenograft for either 7, 14 or 21 days out of a 21 day schedule resulted in significant tumor growth inhibition (TGI) with growth suppression continuing well beyond the period of treatment as compared to vehicle treated animals. Percent tumor growth inhibition was calculated on day 47, which was the final day of treatment for the 21-day treated groups, 7 days post-treatment for 14-day treated groups (14+/7−), or 14-days post treatment for the 7-day treated group (7+/14−).

All groups treated either qd or bid with the 14+/7− schedule resulted in significant tumor growth inhibition, with growth suppression lasting up to 23 days post treatment (day 63). Upon completion of the 21 day cycle on day 47 post tumor implant, the lowest dose of 3 mg/kg compound (1) administered qd resulted in 66% TGI (p<0.001), while the same dose given bid increased the resultant TGI to 83% as compared to vehicle treated control animals (p<0.001). A dose of 10 mg/kg qd produced 77% TGI (p<0.001), and the same dose given bid resulted in 80% TGI (p<0.001). At the maximum tolerated doses of 60 mg/kg qd or 30 mg/kg bid, 88% and 79% TGIs were observed respectively (p<0.001). When a dose of 30 mg/kg qd was given, 79% TGI was obtained as compared to vehicle treated control animals (p<0.001).

When mice were treated with 60 mg/kg compound (1) twice daily with the 7+/14− schedule, treatment initially caused regression of established A549 tumors, while at the end of the 21 day cycle on day 47 post tumor implant, tumor growth inhibition was still 91% as compared to vehicle control mice Inhibition of tumor growth remained prolonged and sustained up to 34 days post treatment (day 67). On day 67, these mice were re-treated with the same dose of compound (1) for a second cycle (7 days) until day 74. Tumor growth continued to be inhibited out to day 90.

Similar results were observed when compound (1) was administered qd or bid consecutively for 21 days, with treatment ending on day 47 post tumor implant. After 21 days of treatment, the lowest dose of 3 mg/kg qd compound (1) yielded 76% TGI (p=0.002), while bid dosing resulted in 83% TGI (p<0.001). Similar to the 14+/7− schedule, mice treated with 10 mg/kg for 21 days resulted in TGIs of 70% (p=0.004) and 72% (p=0.003) respectively for qd and bid treatment groups as compared to vehicle treated controls. Although a dose of 30 mg/kg bid was toxic, it was well tolerated with qd dosing, and A549 tumor growth was inhibited by 66% (p=0.009) as compared to vehicle treated mice. For all 21-day treated groups, inhibition of tumor growth remained prolonged and sustained up to 16 days post treatment (day 63).

It is of note that whether γ-secretase inhibitor compound (1) was dosed qd or bid with either the 14+/7− or full 21 day treatment schedule, there was a general lack of dose response observed with respect to tumor growth inhibition. For example, when compound (1) was dosed qd for 21 days at 3 or 10 mg/kg, the resultant % TGIs were quite similar and not dose proportional, with 76% and 70% TGI respectively. When the same doses of compound (1) were dosed bid (doubling the amount of drug given per day) for 21 days, the % TGIs did not increase proportionately, with 83% and 72% TGI vs. 76% and 70% TGI, respectively.

Growing preclinical evidence has demonstrated that inactivation of the Notch pathway by targeting γ-secretase may be a viable and creditable strategy for the treatment of cancer. Dysregulation of the Notch signaling pathway has been observed in leukemia, T-ALL, medullo- and glioblastoma, breast carcinoma, head and neck cancer, pancreatic carcinoma and many other malignancies. Compound (1) was originally developed for Alzheimer's disease as a potent inhibitor of APP, however here we report the compound's cross-therapeutic application to cancer treatment via inhibition of γ-secretase mediated processing and activation of Notch.

Addition of compound (1) to A549 NSCLC cells in vitro caused a less transformed phenotype as well as loss of the capability for growth in soft agar. To determine the antitumor potential of compound (1) in vivo, nude mice bearing A549 NSCLC xenografts were dosed orally with compound (1) once or twice daily utilizing a 7+/14−, 14+/7−, or full 21 day treatment schedule.

For bid dosing, maximum tolerated doses (MTDs) of 60 mg/kg for 7 days, 30 mg/kg for 14 days, and 10 mg/kg for 21 days were identified. For qd dosing, maximum tolerated doses of 60 mg/kg for 14 days or 30 mg/kg for 21 days were noted. Doses and schedules above the MTDs produced body weight loss and mortality consistent with target-related gastrointestinal toxicity. Earlier histological examination of intestinal crypts with γ-secretase inhibitor treatments revealed dramatic increase in goblet cell differentiation, a known effect of targeting the Notch signaling pathway.

When γ-secretase inhibitor compound (1) was dosed twice daily at 60 mg/kg using the 7+/14− dosing schedule, tumor regression was initially observed, with 91% TGI at the end of the 21 day cycle, and growth suppression continued for several more weeks. After 34 days off treatment, re-initiation with a second cycle of dosing with compound (1) continued repression of tumor growth. Additionally, all other doses of compound (1) (3 mg/kg, 10 mg/kg and 30 mg/kg) given once or twice daily with either the 14+/7− or full 21 day schedules resulted in significant tumor growth inhibition that lasted well beyond the termination of treatment on day 40 or 47 respectively. These data demonstrate that a shorter duration of dosing with compound (1) (i.e. 7 or 14 days) can be as effective in inhibiting A549 tumor growth as dosing for a longer interval (i.e. 21 days).

In many cases, the maximal antitumor effect of compound (1) was delayed and more evident after dosing of the compound has stopped. This preclinical antitumor profile is quite different from classical cytotoxic agents, where maximal tumor growth inhibition is generally observed during the treatment period, and tumors quickly begin to regrow when treatment ceases. Notch is known to be expressed in normal and cancer stem cells, and the delayed antitumor effect observed here is reminiscent of the theoretically predicted delay in tumor shrinkage when cancer stem cells are targeted. Since only a small (but critical) proportion of the tumor's cell population is targeted, once cancer stem cells are terminally differentiated or killed in a tumor, the remaining cells lack the ability for self-renewal and the tumor volume remains stable or gradually decreases.

There was a general lack of dose proportionality observed with respect to tumor growth inhibition, with similar % TGIs at 3, 10, or 30 mg/kg dosed qd for 21 days. Only modest gains in TGI were observed when the daily dose was doubled in bid groups. A comparison of plasma exposures in acute vs. chronically dosed mice with 10 mg/kg compound (1) at the end of the current study demonstrated similar exposures, indicating there was not a loss of exposure over time that might explain the lack of dose proportionality. Further, an independent PK study (PK #1128) in nude mice demonstrated excellent dose proportionality with respect to plasma exposure up to a 30 mg/kg dose [18]. Thus the lack of dose proportionality with respect to tumor growth inhibition is not likely due to saturation of plasma exposure. These results suggest that % TGI is not proportional to exposure, and instead might reflect the unique nature of targeting cancer stem cells rather than rapidly proliferating cells, or simply that there is a biological threshold effect.

Histological analysis of tumor sections stained with H & E did not reveal any differences in tumor cell phenotype with compound (1) treatment, however tumors from mice treated with 10 mg/kg compound (1) for 21 days had increased areas of necrosis and cellular matrix as compared to tumors from vehicle treated mice.

Results of the current study revealed that daily administration of compound (1) was as efficacious as twice daily treatments with either the 14+/7− or 21 day treatment schedule without dose dependency. Moreover, shorter dosing durations (7+/14− or 14+/7−) were as effective in inhibiting A549 tumor growth as dosing for a full 21 days, and the antitumor effect was prolonged well beyond termination of treatment. These data demonstrated that Notch inhibition through administration of the γ-secretase inhibitor, compound (1), may be an effective strategy for cancer treatment.

Example 6

Nonclinical Pharmacology Summary

Compound (1) is a potent and selective inhibitor of -secretase producing inhibitory activity of Notch signaling in tumor cells. Compound (1) produces good in vivo antitumor activity which is maintained after dosing has been stopped with histological analysis showing a unique tumor phenotype consistent with inhibition of Notch signaling.

Compound (1) $IC_{50}$ in cellular and cell-free assays is in the low nanomolar range with a >2 log unit selectivity observed with respect to 75 other binding sites of various types (receptors, ion channels, enzymes). The growth inhibitory activity of compound (1) is complex. Compound (1) does not block tumor cell proliferation nor induce apoptosis but instead produces a less transformed more flattened slower growing phenotype. This mechanism is consistent with Notch inhibition and precludes collecting standard EC50 values. Compound (1) reduces Notch processing as measured by the reduction in ICN expression by Western blot. This leads to reduced expression of the transcriptional target gene product, Hes1, also measured by Western blot.

In in vivo applications, compound (1) is active following oral dosing. Antitumor activity is demonstrated in 3 out of 5 xenografts on an intermittent or daily schedule without body weight loss. Importantly, efficacy is maintained when dosing is terminated. Histological analysis of treated A549 NSCLC tumors shows a tumor phenotype characterized by large areas of necrosis, elevated extracellular matrix. This is consistent with changes in collagen V and MFAP5 protein expression.

These non-clinical pharmacology results support further evaluation of compound (1) in clinical studies in oncology.
Primary Pharmacodynamics
Selectivity In Vitro Multiple in vitro assays were utilized to characterize the potency and selectivity of compound (1). The primary in vitro assay uses cell-free membrane preparations to provide the -secretase enzyme complex as an in vitro assay. Compound (1) strongly inhibits -secretase enzyme activity with 4 nM potency. This translates into potent processing inhibition of the amyloid precursor protein (APP; 14 nM) and Notch (5 nM) in cell-based reporter assays. The cellular processing of APP is measured using an ELISA-based readout. HEK293 cells have been engineered to over-express APP. Processing is measured by an ELISA-based quantitation of the A 1-40 secretase product. Cellular Notch inhibitory activity is measured using HEK293 cell line stably expressing a truncated human Notch 1 fused in its intracellular domain to a VP16/Gal14 transcriptional activator, which drives a firefly luciferase gene Inhibition of Notch processing produces a reduction in luciferase reporter activity as measured by its chemo luminescence.

Mechanistic Studies

The formation of the ICN protein following Notch receptor cleavage by -secretase is a critical step in Notch signaling. ICN moves to the nucleus becoming part of a larger transcriptional complex regulating the transcription of various target genes including Hes1. The reduction of ICN expression and the Notch target gene product, Hes1, in tumor cell lines was monitored by Western blot. Compound (1) suppresses the production of ICN inducing a flattened less transformed tumor cell phenotype in tissue culture after five days of treatment in the human NSCLC A549 cells. Treatment with compound (1) produces a flattened, non-transformed phenotype in tissue culture. This data is consistent with inhibiting γ-secretase in tumor cells. The appearance of an apoptotic phenotype following compound treatment was not observed.

The ability to form colonies in soft agar represents a critical event in tumor cell progression. Non-transformed cells and poorly tumorigenic cells fail to grow when plated in soft agar. In contrast, highly tumorigenic cells grow rapidly under soft agar conditions producing large colonies. The effect of compound (1) on the transformed phenotype was evaluated in the human breast cancer cell line MDA-MB-468 by measuring growth potential in soft agar. Compound (1) reduced colony growth in a dose-dependent manner (250 nM>100 nM>control).

In Vivo Evaluations

The pre-clinical anti-tumor activity was tested in several xenograft models utilizing various doses and schedules. In the A549 NSCLC model, compound (1) gave statistically significant tumor growth inhibition (70% TGI) in nude mice treated QD for 21 days (Table 5). Body weight loss was used as a surrogate for overall tolerability of compound (1) following long term dosing during efficacy testing. Exposures producing efficacy (AUC24/day) were approximately 1100 h·ng/ml on an oral daily dosing schedule of 10 mg/kg and did not result in body weight loss or show clinical signs of toxicity. No loss of exposure was observed between day 1 and 21 day following continuous daily dosing. The histological analysis of tumors harvested at the end of this study revealed large areas of necrosis with an increase in extracellular matrix.

Compound (1) is orally active in 3/4 established tumor models predicted to be sensitive (based on the level of endogenous Notch signaling) in nude mice dosed below the MTD on a daily schedule for twenty-one days (Table 5). It is inactive in 1/1 model predicted to be insensitive. Efficacious response may correlate with the tumor Notch1/Notch3 expression ratio. Notch3 reportedly acts as a negative regulator of Notch1 by competing with the Notch1 ICN for nuclear transcription factors. Preliminary data shows elevated expression of the Notch3 protein in the non-responsive xenograft cell line and reduced expression in the sensitive cell lines.

Compound (1) is Orally Active in 3/4 Xenograft Models Predicted to be Sensitive and Inactive in 1/1 Models Predicted to be Insensitive

| Xenograft model | 3 mg/kg qd × 21 days (% TGI) | 10 mg/kg qd × 21 days (% TGI) | 30 mg/kg qd × 7 days (% TGI) | 60 mg/kg qd × 7 days (% TGI) |
|---|---|---|---|---|
| A549 NSCLC | 76 | 70 | — | — |
| Calu-6 NSCLC | †59 | †42 | #34 | #52 |
| LOVO colon | †40 | †83 | #59 | #85 |
| HCT-116 colon | *85 | *76 | ¶63 | ¶90 |
| H460a NSCLC | 0 | 0 | 0 | 0 |

NSCLC = non-small cell lung cancer.
Efficacy = % TGI ≥ 60 and p ≤ 0.05 as compared to vehicle control group.
*maximal TGI when 21-day treatment ended.
†maximal TGI one week after 21-day treatment ended (21+/7−).
maximal TGI after $2^{nd}$ round of 7-day treatment (7+/14−/7+).
¶maximal TGI 5 days after $2^{nd}$ round of 7-day treatment (7+/14−/7+/5−).

Additional dose and scheduling studies in the A549 model produced statistically significant tumor growth inhibition between 79-91% after seven days or fourteen days of BID treatment out of a 21 day treatment cycle without body weight loss. The seven-day treatment group was monitored for an additional forty-three days. The tumor growth remained stable throughout the observation period. Seven days of dosing was reinitiated at day sixty-six producing tumor growth inhibition out to day 90. The pattern of efficacy observed in mice with compound (1) is unique compared to that observed with other cancer therapeutics in that the maximal efficacy has sometimes been delayed a week or two following cessation of treatment, and prolonged efficacy has also been observed following treatment. This type of response is consistent with Notch inhibition. Both continuous daily and intermittent schedules are efficacious without body weight loss. Compound (1) is suitable for cyclical dosing. This data supports the concept of the intermittent dosing proposed for Phase 1. Such a schedule may help to reduce potential toxicity and CYP3A4 impact anticipated from daily dosing in humans.

Exposures ($AUC_{24h}$) producing efficacy were approximately 1100 ng*hr/mL on an oral daily dosing schedule of 10 mg/kg and did not result in body weight loss or show clinical signs of toxicity. No loss of exposure was observed between days 1 and 21 of daily dosing consistent with a lack of induction in metabolism following repeated doses. The lack of change in exposure following long term dosing was also observed during rat and dog studies.

In Vivo Mechanistic Studies

Microarray analysis of -secretase inhibitor treated A549 xenograft tumors revealed RNA expression changes consistent with the extracellular matrix alteration. Compound (1) treated tumors treated were prepared for Western blot analysis. Collagen type V expression was significantly reduced while MFAP5 protein expression was elevated. Notch-1 protein levels and the expression of the ICN were reduced in all animal groups except for the highest dose group. Collagen type V and MFAP5 are structural proteins that make up the extracellular matrix. Collagen type V expression is often reduced and MFAP5 expression is often elevated in more differentiated tissues. This data is consistent with the working hypothesis that Notch-1 inhibition in A549 tumor cells leads to a more differentiated phenotype.

Example 7

Antitumor Activity in Human Pancreatic Cancer Xenografts

Animals

Female (athymic nu/nu) nude mice were obtained from Charles River Laboratories (Wilmington, Mass.), while female SCID-beige mice were purchased from Taconic (Germantown, N.Y.). Mice were used when they were approximately 8-12 weeks old (nudes) or 8-10 weeks old (SCID-beige), and weighed approximately 23-25 grams. The health of all animals was determined daily by gross observation of experimental animals and by the analyses of blood samples of sentinel animals that were housed on the shared shelf racks. All animals were allowed to acclimate and recover from any shipping related stress for a minimum of 72 hours prior to experimental use. Autoclaved water and irradiated food [5058-ms Pico chow (mouse) Purina, Richmond, Ind.] were provided ad libitum, and the animals were maintained on a 12 hour light and dark cycle. Cages, bedding and water bottles were autoclaved before use and were changed weekly.

Tumors

MiaPaca2, AsPC1 and BxPC3 human pancreatic carcinoma cells were purchased from ATCC (Manassas, Va.). BxPC3 and AsPC1 cells were grown in RPMI medium and MiaPaca2 cells were grown in Dulbecco's Modified Essential Medium (DMEM). All culture media were supplemented with 10% (v/v) FBS and 1% (v/v) 200 nM L-glutamine. Nude mice were implanted se with $6\times10^6$ MiaPaca2 cells or $5\times10^6$ AsPC1 cells in a volume of 0.2 ml of PBS per mouse in the right hind flank on Jan. 22, 2007 and Mar. 14, 2007 respectively. SCID-biege mice were implanted se with $5\times10^6$ BxPC3 cells in a 1:1 mixture of matrigel:PBS in a volume of 0.2 ml per mouse in the right hind flank on May 22, 2007.

Test Agents

Compound (1) was formulated by as a suspension in 1.0% Klucel in water with 0.2% Tween-80 for oral (po) administration. Formulated compound and vehicle were stored at 4° C. and prepared weekly. The suspension was mixed vigorously prior to administration. Gemcitabine (Gemzar®, Eli Lilly and Company, Indianapolis, Ind., USA) was reconstituted with sterile saline to yield a stock solution of 38 mg/ml for the entire 3-4 week study. Further dilution of gemcitabine to give the desired concentration for in vivo administration was made with sterile saline on the day of dosing.

Randomization

Nude mice implanted with MiaPaca2 or AsPC1 xenografts were randomized on day 17 and day 9 post cell implant, respectively. SCID-beige mice bearing BxPC3 xenografts were randomized 8 days post implant. All mice were randomized according to tumor volume, so that all groups had similar starting mean tumor volumes of approximately 100-150 mm³

Treatment Initiation

Treatment for the MiaPaca2 study began on Feb. 8, 2007 (day 17 post tumor implant), for AsPC1 on Mar. 23, 2007 (day 9 post tumor implant), and for the BxPC3 study on May 30, 2007 (day 8 post tumor implant). Oral vehicle or the Compound (1) suspension was dosed using a sterile 1 cc syringe and 18-gauge gavage needle (0.2 ml/animal) once daily (qd) for 21-28 days, or using an intermittent schedule (7 days on, 7 days off, 7 days on (7+/7−/7+), 7 days on, 7 days off (7+/7−), 3 days on, 4 days off (3+/4−), or 14 days on, 14 days off (14+/14−)). Gemcitabine was administered to the mice intraperitoneally (ip) q3d (every 3 days) using a 1 cc syringe and 26 gauge needle.

For the MiaPaca2 and AsPC1 studies, qd Compound (1) suspension or q3d gemcitabine treatment ended on day 37 post tumor cell implant, whereas for the BxPC3 study, qd Compound (1) suspension or q3d gemcitabine treatment ended on day 35 post tumor cell implant.

For intermittent dosing of Compound (1) suspension in the MiaPaca2 study using the 7+/7−/7+ schedule, treatment ended on day 23, was reinitiated on day 31, and ended day 37. In the combination groups Compound (1) suspension was given sequentially with gemcitabine using the 7+/7−/7+ schedule so that Compound (1) was dosed daily only during the first and third weeks, whereas gemcitabine was dosed q3d during the second week only.

For intermittent dosing of Compound (1) suspension in the AsPC1 study using the 7+/7− schedule×2 cycles, treatment ended on day 15, was reinitiated on day 23, and finally ended day 29. For intermittent dosing using the 3+/4− schedule×4 cycles, treatment ended on day 11, was reinitiated on day 16, ended day 18, was reinitiated on day 23, ended day 25, was reinitiated day 30, and finally ended on day 32. In the first combination group, daily Compound (1) was given simultaneously with q3d gemcitabine for a total of four weeks. For the remaining combination groups, Compound (1) and gemcitabine were given sequentially rather than simultaneously. In group 8 gemcitabine was dosed q3d during the $1^{st}$ and $3^{rd}$ weeks, whereas Compound (1) was given daily during the $2^{nd}$ and $4^{th}$ weeks only. In group 9, the order of compound dosing was reversed, with Compound (1) suspension given daily during the $1^{st}$ and $3^{rd}$ weeks, whereas gemcitabine was given q3d during the $2^{nd}$ and $4^{th}$ weeks. In group 10, gemcitabine was dosed q3d during the $1^{st}$ and $2^{nd}$ weeks, whereas Compound (1) was given daily during the $3^{rd}$ and $4^{th}$ weeks. In group 11, the order of compound dosing was reversed, with Compound (1) given daily during the $1^{st}$ and $2^{nd}$ weeks, and gemcitabine dosed q3d for the $3^{rd}$ and $4^{th}$ weeks.

Upon termination of treatment, in all three studies, tumor-bearing mice were callipered for an additional follow-up period in order to evaluate tumor re-growth. For the MiaPaca2 study the follow-up period lasted until day 63 (26 days post-treatment), for AsPC1 until day 48 (11 days post-treatment), and for BxPC3 until day 50 (15 days post-treatment).

Calculations & Statistical Analysis

Weight loss was graphically represented as percent change in mean group body weight, using the formula: $((W-W_0)/W_0)\times100$, where 'W' represents mean body weight of the treated group at a particular day, and 'W0' represents mean body weight of the same treated group at initiation of treatment. Maximum weight loss was also represented using the above formula, and indicated the maximum percent body weight loss that was observed at any time during the entire experiment for a particular group. Toxicity is defined as ≥20% of mice in a given group demonstrating ≥20% body weight loss and/or mortality.

Efficacy data was graphically represented as the mean tumor volume+standard error of the mean (SEM). Tumor volumes of treated groups were presented as percentages of tumor volumes of the control groups (% T/C), using the formula: $100\times((T-T_0)/(C-C_0))$, where T represented mean tumor volume of a treated group on a specific day during the experiment, $T_0$ represented mean tumor volume of the same treated group on the first day of treatment; C represented mean tumor volume of a control group on the specific day during the experiment, and $C_0$ represented mean tumor volume of the same treated group on the first day of treatment. Tumor volume (in cubic millimeters) was calculated using the ellipsoid formula: $(D\times(d2))/2$ where 'D' represents the large diameter of the tumor, and 'd' represents the small diameter. In some cases, tumor regression and/or percent change in tumor volume was calculated using the formula: $((T-T_0)/T_0)\times100$ where 'T' represents mean tumor volume of the treated group at a particular day, and '$T_0$' represents mean tumor volume of the same treated group at initiation of treatment. Statistical analysis was determined by the rank sum test and One Way Anova and a post-hoc Bonferroni t-test (SigmaStat, version 2.0, Jandel Scientific, San Francisco, Calif.).

Differences between groups were considered to be significant when the probability value (p) was ≤0.05.

For survival assessment, results are plotted as the percentage survival against days after tumor implant (StatView, SAS Institute, Cary N.C.). The % ILS was calculated as 100× [(median survival day of treated group−median survival day of control group)/median survival day of control group]. Median survival was determined utilizing Kaplan Meier survival analysis. Survival in treated groups was compared with the vehicle group by log-rank test, and survival comparisons between groups were analyzed by the Breslow-Gehan-Wilcoxon test (StatView, SAS, Cary, N.C.). Differences between groups were considered significant when the probability value (p) was ≤0.05.

Results

Toxicity

In all three studies (MiaPaca2, AsPC1, and BxPC3) all doses and schedules of Compound (1) or gemcitabine given alone or in combination were well tolerated as defined by <20% of animals exhibiting ≥20% body weight loss, morbidity, or death. In the MiaPaca2 study, one mouse each in the 60 mg/kg q3d gemcitabine and 30 mg/kg 7+/7−/7+ Compound (1) groups died due to misdosing. In the AsPC1 study, one mouse in the 90 mg/kg gemcitabine single agent group was euthanized on day 22 due to >20% body weight loss, which was deemed toxicity related due to progressive body weight loss over the course of a week. In the BxPC3 study, one mouse in the 10 mg/kg qd group exhibited >20% body weight loss (bwl) on the last day of the study, which was also deemed toxicity-related since the mouse exhibited progressive body weight loss during the last few weeks of the study.

Efficacy

When Compound (1) was administered to mice bearing MiaPaca2 human pancreatic carcinoma xenografts, biologically significant tumor growth inhibition (TGI) (as defined by the NCI as ≥60% TGI) could not be achieved irrespective of the dose or schedule, alone or in combination with gemcitabine [11]. Administration of Compound (1) for 21 consecutive days (qd) to nude mice bearing MiaPaca2 xenografts resulted in statistically significant, but not biologically significant tumor growth inhibition (TGI) when compared to vehicle treated controls. Amongst the qd groups, a dose response was observed with 1 mg/kg resulting in 39% TGI (p=0.002), 3 mg/kg yielding 42% TGI (p=0.002), and 10 mg/kg inhibiting tumor growth by 53% as compared to vehicle treatment (p<0.001). In the groups where Compound (1) was administered intermittently on a schedule of 7+/7−/7+ days (dosed daily the $1^{st}$ and $3^{rd}$ weeks), all three doses demonstrated similar growth inhibition that was not biologically significant, indicating a lack of dose response with the schedule. The highest dose of 60 mg/kg inhibited tumor growth by 48% (p≤0.001), whereas the 10 mg/kg and 30 mg/kg doses of Compound (1) resulted in 51% TGI (p≤0.001) and 58% TGI (p≤0.001), respectively. When gemcitabine was administered q3d at 60 mg/kg, 62% TGI was observed as compared to vehicle treated controls (p≤0.001). In the combination groups, antitumor activity was neither biologically significant nor statistically different from the respective Compound (1) monotherapy arms, with 57% or 54% TGI in the gemcitabine plus Compound (1) 10 mg/kg or 30 mg/kg 7+/7−/7+ groups. After cessation of treatment, tumor growth was monitored for a follow-up period of 26 days (up to day 63). On day 63, TGI values for all groups were lower than on day 37, indicating that MiaPaca2 tumors re-grew post-treatment.

Similar to the MiaPaca2 study, when Compound (1) was administered to mice bearing AsPC1 human pancreatic carcinoma xenografts as a monotherapy, biologically significant tumor growth inhibition could not be achieved irrespective of the dose or schedule. On the other hand, when Compound (1) was given in combination with gemcitabine, biologically significant tumor growth inhibition was achieved when both drugs were given simultaneously, or when given sequentially if gemcitabine was given first for two weeks. Administration of Compound (1) for 28 consecutive days (qd) to nude mice bearing AsPC1 xenografts resulted in statistically significant, but not biologically significant tumor growth inhibition (TGI) when compared to vehicle treated controls. At doses of 3 mg/kg and 10 mg/kg qd, 49% (p=0.004) and 58% TGI (p=0.004) were observed, respectively as compared to vehicle treated mice. When Compound (1) (10 mg/kg) was dosed intermittently (3+/4−×4 cycles or 7+/7−×2 cycles), the antitumor activity was lessened as compared to continuous daily dosing (TGI=32% and 41%, respectively). Gemcitabine dosed q3d at 90 mg/kg displayed very little antitumor activity in the AsPC1 pancreatic model, with only 39% TGI (p=0.016) as compared to vehicle control. Conversely, when Compound (1) was combined in simultaneous administration with gemcitabine, an enhanced effect on antitumor activity was observed, with 77% TGI (p≤0.001). This result was both biologically significant and statistically significant as compared to the gemcitabine monotherapy arm (p=0.005), but not the Compound (1) monotherapy arm (p=0.251). In weekly sequenced combination groups, although administration of gemcitabine prior to Compound (1) inhibited AsPC1 tumor growth better than the reverse order, (58% TGI, p≤0.001 vs. 37%, p=0.012), neither result was biologically significant. In the two-week sequenced combination groups, administration of gemcitabine prior to Compound (1) again inhibited AsPC1 tumor growth better than the reverse order, however in this case the antitumor activity was biologically significant, with 70% TGI (p≤0.001) Vs. 55% TGI (p≤0.001). AsPC1 tumor growth was monitored for 11 days post-cessation of treatment (up to day 48). On day 48, TGI values for all groups were lower than on day 37, indicating that AsPC1 tumors re-grew post-treatment.

In contrast to the lack of robust tumor growth suppression elicited by Compound (1) monotherapy in the MiaPaca2 and AsPC1 pancreatic xenograft models, the BxPC3 pancreatic xenograft model was sensitive to Compound (1) mediated growth inhibition. Administration of 3 mg/kg and 10 mg/kg Compound (1) significantly inhibited BxPC3 tumor growth (biologically and statistically) in a dose-dependent fashion, with 72% (p<0.001) and 82% TGI (p<0.001) respectively, as compared to vehicle controls. Similarly, most intermittent dosed groups also yielded statistically and biologically significant tumor growth inhibition, although a lack of dose response was observed. When Compound (1) was dosed using the 7+/7− schedule, doses of 10 mg/kg and 20 mg/kg yielded 74% (p≤0.001) and 63% TGI (p=0.002) respectively, as compared to vehicle treated control mice. Compound (1) was also dosed using the 3+/4− schedule, where doses of 10 mg/kg, 23 mg/kg, and 30 mg/kg inhibited tumor growth by 56% (p=0.002) 64% (p<0.001), and 50% (p=0.024), respectively. BxPC3 tumor growth was monitored for 15 days post-cessation of treatment (up to day 50). On day 50, TGI values for daily dosed groups were similar to day 35, indicating that Compound (1) elicited sustained tumor growth inhibition in the BxPC3 pancreatic model.

The Notch signaling pathway has been implicated in the pathogenesis of pancreatic cancer. In the current study, the gamma secretase inhibitor (Compound 1) was administered orally for up to four weeks to mice bearing established sc MiaPaca2, AsPC1 or BxPC3 pancreatic tumors, alone or in combination with Gemcitabine. Compound (1) elicited biologically significant antitumor activity (as defined by the NCI as ≥60% TGI) as a monotherapy in one out of the three pancreatic tumor models. The BxPC3 model was sensitive to Compound (1) mediated growth inhibition whether compound was administered daily or intermittently with either a 7+/7− or 3+/4− schedule. The degree of tumor growth inhibition was dependent on dose when Compound (1) was given daily, whereas antitumor activity seemed independent of dose when given on an intermittent schedule. When comparing the total amount of drug given per month on the various dosing schedules, daily dosing yielded superior efficacy. For example, when a total monthly dose of 280 mg/kg split either into a schedule of 10 mg/kg given qd, 10 mg/kg given 7+/7−, or 23 mg/kg given 3+/4−, antitumor activity was superior with daily dosing (82% Vs. 63% or 64% TGI, respectively). BxPC3 tumor growth was monitored for 15 days post-cessation of treatment, during which time TGI values for daily dosed groups remained stable, indicating that Compound (1) elicited sustained tumor growth inhibition in the BxPC3 pancreatic model.

Although Compound (1) did not produce biologically significant efficacy in the MiaPaca2 or AsPC1 pancreatic tumor models as a monotherapy, it did enhance the antitumor activity of gemcitabine when given in combination in the AsPC1 model. The combination of 10 mg/kg qd Compound (1) plus 90 mg/kg gemcitabine q3d given simultaneously produced 77% TGI as compared to either 58% or 39% with Compound (1) or gemcitabine monotherapy, respectively. When the combination of Compound (1) and gemcitabine was given in sequence rather than simultaneously, only the two-week sequenced combination where gemcitabine was given prior to Compound (1) produced biologically significant tumor growth inhibition, with 70%. TGI observed. On the other hand, when the two drugs were given in reverse order, only 55% TGI was observed.

While the BxPC3, MiaPaca2, and AsPC1 pancreatic tumor models differ in their expression of Notch receptors, ligands, and downstream targets, no obvious differences could be easily correlated with their sensitivity to the gamma secretase inhibitor. For example, all three cell lines express low levels of Notch-1, BxPC3 and AsPC1 express low levels of Notch-2, whereas MiaPaca2 expresses very high levels of Notch-2 and is also the only cell line that expresses Notch 3 and 4 [12]. All three cell lines express the ligand Jagged-1, with AsPC1 cells expressing the highest level, followed by BxPC3, and Mia-Paca2 expressing the lowest level. The ligands Jagged-2 and Delta-1 are expressed in BxPC3 and MiaPaca2 cells, but not in AsPC1 cells [12]. Although there is some data in the literature to suggest activating mutations in K-Ras may cooperate with Notch in transforming cells, in the present studies, the only tumor model sensitive to g secretase mediated growth inhibition was wild-type for K-Ras (BxPC3).

In the present in vivo studies, it is demonstrated that Compound (1) can effectively inhibit tumor growth in some pancreatic tumor models as a monotherapy or in combination with gemcitabine, however the mechanisms for differential sensitivity between models remains poorly understood.

While a number of embodiments of this invention have been represented, it is apparent that the basic construction can be altered to provide other embodiments that utilize the invention without departing from the spirit and scope of the invention. All such modifications and variations are intended to be included within the scope of the invention as defined in the appended claims rather than the specific embodiments that have been presented by way of example.

The invention claimed is:

1. A method for treating a patient having cancer comprising administering to the patient a therapeutically effective amount of compound (1), or a pharmaceutically acceptable salt thereof, having the formula:

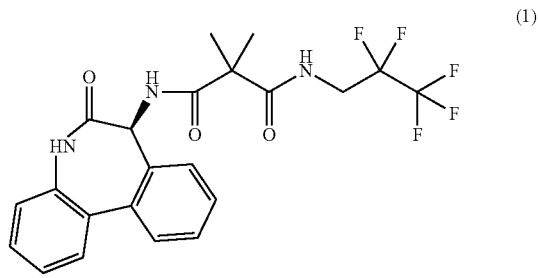 [SMILES: CC(C)(C(=O)NCC(F)(F)C(F)(F)F)C(=O)N[C@@H]1C(=O)Nc2ccccc2-c2ccccc21]

wherein the cancer is non-small cell lung cancer or colon cancer.

2. The method of claim 1, wherein the therapeutically effective amount of compound (1) is from about 400 ng-hr/ml to about 9000 ng-hr/ml.

3. The method of claim 2, wherein the therapeutically effective amount of compound (1) is from about 1100 ng-hr/ml to about 4100 ng-hr/ml.

4. The method of claim 3, wherein the therapeutically effective amount of compound (1) is from about 1380 ng-hr/ml to about 2330 ng-hr/ml.

5. The method of claim 2, wherein the therapeutically effective amount of compound (1) is from about 400 ng-hr/ml to about 9000 ng-hr/ml administered over a period of up to about 21 days.

6. The method of claim 3, wherein the therapeutically effective amount of compound (1) is from about 1100 ng-hr/ml to about 4100 ng-hr/ml administered over a period of up to about 21 days.

7. The method of claim 4, wherein the therapeutically effective amount of compound (1) is from about 1380 ng-hr/ml to about 2330 ng-hr/ml administered over a period of up to about 21 days.

8. The method of claim 1, wherein compound (1) is administered once daily on days 1, 2, 3, 8, 9, and 10 of a 21 day cycle.

9. The method of claim 8, wherein compound (1) is administered once daily on days 1, 2, 3, 8, 9, and 10 of a 21 day cycle in an amount of from about 400 ng-hr/ml to about 9000 ng-hr/ml.

10. The method of claim 1, wherein compound (1) is administered once daily on days 1-7 of a 21 day cycle.

11. The method of claim 10, wherein compound (1) is administered once daily on days 1-7 of a 21 day cycle in an amount of from about 400 ng-hr/ml to about 9000 ng-hr/ml.

12. The method of claim 1, wherein compound (1) is in a pharmaceutical oral unit dosage form.

13. The method of claim 1, comprising additionally subjecting the patient to radiotherapy.

14. A method for treating a patient having cancer comprising administering to the patient a therapeutically effective amount of compound (1), or a pharmaceutically acceptable salt thereof, having the formula:

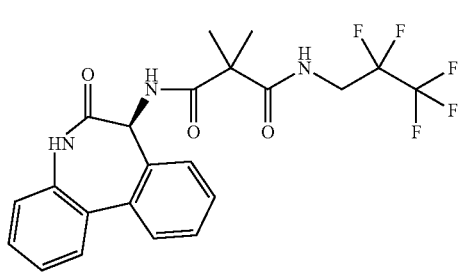
(1)

wherein compound (1) is administered once daily on days 1, 2, 3, 8, 9, and 10 of a 21 day cycle in an amount of from about 400 ng-hr/ml to about 9000 ng-hr/ml;
wherein the cancer is non-small cell lung cancer or colon cancer.

15. A method for treating a patient having cancer comprising administering to the patient a therapeutically effective amount of compound (1), or a pharmaceutically acceptable salt thereof, having the formula:

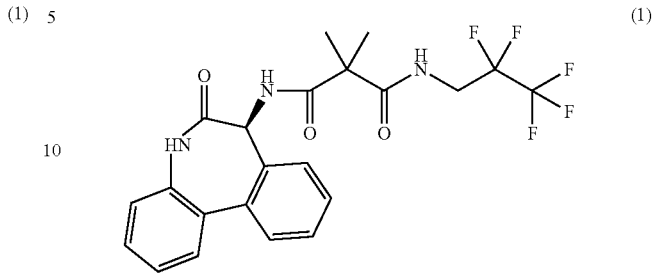
(1)

wherein compound (1) is administered once daily on days 1-7 of a 21 day cycle in an amount of from about 400 ng-hr/ml to about 9000 ng-hr/ml;
wherein the cancer is non-small cell lung cancer or colon cancer.

* * * * *